(12) United States Patent
Bunker et al.

(10) Patent No.: US 12,049,460 B2
(45) Date of Patent: *Jul. 30, 2024

(54) EGFR INHIBITOR COMPOUNDS

(71) Applicant: Recurium IP Holdings, LLC, San Diego, CA (US)

(72) Inventors: Kevin Duane Bunker, Escondido, CA (US); Peter Qinhua Huang, San Diego, CA (US); Sunny Abraham, San Diego, CA (US); Joseph Robert Pinchman, San Diego, CA (US); Chad Daniel Hopkins, San Diego, CA (US); Deborah Helen Slee, Encinitas, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 17/445,280

(22) Filed: Aug. 17, 2021

(65) Prior Publication Data

US 2021/0395230 A1 Dec. 23, 2021

Related U.S. Application Data

(60) Continuation of application No. 16/703,544, filed on Dec. 4, 2019, now Pat. No. 11,098,030, which is a division of application No. 15/603,789, filed on May 24, 2017, now Pat. No. 10,513,509.

(60) Provisional application No. 62/342,141, filed on May 26, 2016.

(51) Int. Cl.
| | |
|---|---|
| *C07D 403/04* | (2006.01) |
| *A61K 31/506* | (2006.01) |
| *A61P 35/00* | (2006.01) |
| *C07C 13/36* | (2006.01) |
| *C07D 209/04* | (2006.01) |
| *C07D 403/14* | (2006.01) |
| *C07D 471/04* | (2006.01) |

(52) U.S. Cl.
CPC .......... *C07D 403/04* (2013.01); *A61K 31/506* (2013.01); *A61P 35/00* (2018.01); *C07C 13/36* (2013.01); *C07D 209/04* (2013.01); *C07D 403/14* (2013.01); *C07D 471/04* (2013.01)

(58) Field of Classification Search
CPC .................................................. C07D 403/04
See application file for complete search history.

(56) References Cited

U.S. PATENT DOCUMENTS

| | | |
|---|---|---|
| 5,463,071 A | 10/1995 | Himmelsbach et al. |
| 10,513,509 B2 | 12/2019 | Bunker et al. |
| 11,098,030 B2 | 8/2021 | Bunker et al. |
| 2005/0089935 A1 | 4/2005 | Cai et al. |
| 2011/0108766 A1 | 5/2011 | Akino |
| 2012/0028924 A1 | 2/2012 | Aquila et al. |
| 2012/0214762 A1 | 8/2012 | Staben et al. |
| 2013/0053409 A1 | 2/2013 | Butterworth et al. |
| 2013/0196972 A1 | 8/2013 | Chung et al. |
| 2014/0141000 A1 | 5/2014 | Chiu et al. |
| 2015/0071919 A1 | 3/2015 | White et al. |
| 2016/0045436 A1 | 2/2016 | Mohr et al. |
| 2016/0340356 A1 | 11/2016 | Fan et al. |
| 2016/0355503 A1 | 12/2016 | Zhou et al. |
| 2017/0008889 A1 | 1/2017 | Lan et al. |
| 2017/0088543 A1 | 3/2017 | Astrand et al. |
| 2017/0115275 A1 | 4/2017 | Rege et al. |
| 2017/0121321 A1 | 5/2017 | Crews et al. |
| 2017/0121326 A1 | 5/2017 | Schiltz et al. |
| 2017/0196835 A1 | 7/2017 | Talley et al. |
| 2017/0224654 A1 | 8/2017 | Armstrong et al. |
| 2017/0342055 A1 | 11/2017 | Bunker et al. |
| 2017/0355696 A1 | 12/2017 | Jiang |

(Continued)

FOREIGN PATENT DOCUMENTS

| | | |
|---|---|---|
| CN | 104140418 | 11/2014 |
| CN | 104761544 | 7/2015 |
| CN | 104761585 | 7/2015 |

(Continued)

OTHER PUBLICATIONS

Ali et al., "Antitumor Response of an ERBB2 Amplified Inflammatory Breast Carcinoma with EGFR Mutation to the EGFR-TKI Erlotinib" Clinical Breast Cancer (2014) 14(1):e14.

(Continued)

*Primary Examiner* — Brian E McDowell
(74) *Attorney, Agent, or Firm* — Knobbe Martens Olson & Bear LLP

(57) ABSTRACT

Disclosed herein are nitrogen-containing bicyclic compounds of Formula (I), including pharmaceutically acceptable salts thereof, together with pharmaceutical compositions and methods of ameliorating and/or treating a cancer described herein with one or more of the compounds described herein.

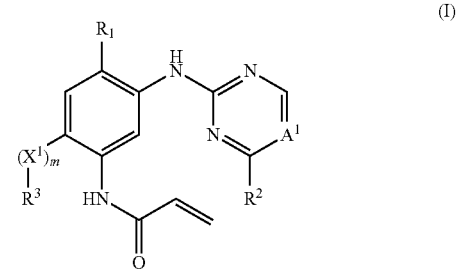

20 Claims, No Drawings

(56) References Cited

U.S. PATENT DOCUMENTS

2020/0181120 A1 6/2020 Bunker et al.

FOREIGN PATENT DOCUMENTS

| | | |
|---|---|---|
| CN | 104817541 | 8/2015 |
| CN | 104844580 | 8/2015 |
| CN | 104860941 A | 9/2015 |
| CN | 104876914 | 9/2015 |
| CN | 104892585 | 9/2015 |
| CN | 104910049 | 9/2015 |
| CN | 105126125 | 9/2015 |
| CN | 104961731 | 10/2015 |
| CN | 105001208 | 10/2015 |
| CN | 105085489 | 11/2015 |
| CN | 105153122 | 12/2015 |
| CN | 105237515 | 1/2016 |
| CN | 105254615 | 1/2016 |
| CN | 105294717 | 2/2016 |
| CN | 105348267 | 2/2016 |
| CN | 105461695 | 4/2016 |
| CN | 105461729 | 4/2016 |
| CN | 105585557 | 5/2016 |
| CN | 105601620 | 5/2016 |
| CN | 105646454 | 6/2016 |
| CN | 105777716 | 7/2016 |
| CN | 105886648 | 8/2016 |
| CN | 105985323 | 10/2016 |
| CN | 106138020 | 11/2016 |
| CN | 106138061 | 11/2016 |
| CN | 106366022 | 2/2017 |
| CN | 106366072 | 2/2017 |
| CN | 106397407 | 2/2017 |
| CN | 106432231 | 2/2017 |
| CN | 106699736 | 2/2017 |
| CN | 106478605 | 3/2017 |
| CN | 106496196 | 3/2017 |
| CN | 106543060 | 3/2017 |
| CN | 106565522 | 4/2017 |
| CN | 106668866 | 5/2017 |
| CN | 106674202 | 5/2017 |
| CN | 106883216 | 6/2017 |
| EA | 201391491 A1 | 8/2014 |
| RU | 2536584 C2 | 12/2014 |
| WO | WO 95/09847 | 4/1995 |
| WO | WO 97/44326 | 11/1997 |
| WO | WO 2005/123672 | 12/2005 |
| WO | WO 2006/026754 | 3/2006 |
| WO | WO 2006/050076 | 5/2006 |
| WO | WO 2006/075152 | 7/2006 |
| WO | WO 2006/096564 | 9/2006 |
| WO | WO 2007/042806 | 4/2007 |
| WO | WO 2007/149427 | 12/2007 |
| WO | WO 2008/024978 | 2/2008 |
| WO | WO 2008/137105 | 11/2008 |
| WO | WO 2009/157428 | 12/2009 |
| WO | WO 2009/158571 | 12/2009 |
| WO | WO 2010/020432 | 2/2010 |
| WO | WO 2010/051781 | 5/2010 |
| WO | WO 2011/019780 | 2/2011 |
| WO | WO 2011/031896 | 3/2011 |
| WO | WO 2011/052888 | 5/2011 |
| WO | WO 2012/050393 | 4/2012 |
| WO | WO 2012/126181 | 9/2012 |
| WO | WO 2013/014448 | 1/2013 |
| WO | WO 2013/074986 | 5/2013 |
| WO | WO 2013/155223 | 10/2013 |
| WO | WO 2014/000418 | 1/2014 |
| WO | WO 2014/047662 | 3/2014 |
| WO | WO 2014/063068 | 4/2014 |
| WO | WO 2014/081944 | 5/2014 |
| WO | WO 2014/178606 | 11/2014 |
| WO | WO 2015/030847 | 3/2015 |
| WO | WO 2015/049280 | 4/2015 |
| WO | WO 2015/101791 | 7/2015 |
| WO | WO 2015/112705 | 7/2015 |
| WO | WO 2015/127234 | 8/2015 |
| WO | WO 2015/127872 | 9/2015 |
| WO | WO 2015/134242 | 9/2015 |
| WO | WO 2015/150826 | 10/2015 |
| WO | WO 2015/154039 | 10/2015 |
| WO | WO 2015/175965 | 11/2015 |
| WO | WO 2015/188777 | 12/2015 |
| WO | WO 2015/195228 | 12/2015 |
| WO | WO 2016/005593 | 1/2016 |
| WO | WO 2016/011979 | 1/2016 |
| WO | WO 2016/023422 | 2/2016 |
| WO | WO 2016/024185 | 2/2016 |
| WO | WO 2016/029839 | 3/2016 |
| WO | WO 2016/032003 | 3/2016 |
| WO | WO 2016/038609 | 3/2016 |
| WO | WO 2016/038610 | 3/2016 |
| WO | WO 2016/040622 | 3/2016 |
| WO | WO 2016/045799 | 3/2016 |
| WO | WO 2016/054987 | 4/2016 |
| WO | WO 2016/058544 | 4/2016 |
| WO | WO 2016/060443 | 4/2016 |
| WO | WO 2016/070816 | 5/2016 |
| WO | WO 2016/090174 | 6/2016 |
| WO | WO 2016/094821 | 6/2016 |
| WO | WO 2016/105582 | 6/2016 |
| WO | WO 2016/112272 | 7/2016 |
| WO | WO 2016/112302 | 7/2016 |
| WO | WO 2016/125169 | 8/2016 |
| WO | WO 2016/126085 | 8/2016 |
| WO | WO 2016/141324 | 9/2016 |
| WO | WO 2016/164217 | 10/2016 |
| WO | WO 2016/170157 | 10/2016 |
| WO | WO 2016/185333 | 11/2016 |
| WO | WO 2016/191471 | 12/2016 |
| WO | WO 2016/197012 | 12/2016 |
| WO | WO 2016/201370 | 12/2016 |
| WO | WO 2017/009258 | 1/2017 |
| WO | WO 2017/011907 | 1/2017 |
| WO | WO 2017/013160 | 1/2017 |
| WO | WO 2017/015008 | 1/2017 |
| WO | WO 2017/015363 | 1/2017 |
| WO | WO 2017/016463 | 2/2017 |
| WO | WO 2017/031036 | 2/2017 |
| WO | WO 2017/067447 | 4/2017 |
| WO | WO 2017/086830 | 5/2017 |
| WO | WO 2017/086831 | 5/2017 |
| WO | WO 2017/096095 | 6/2017 |
| WO | WO 2017/096100 | 6/2017 |
| WO | WO 2017/100642 | 6/2017 |
| WO | WO 2017/111074 | 6/2017 |
| WO | WO 2017/114500 | 7/2017 |
| WO | WO 2017/117070 | 7/2017 |
| WO | WO 2017/120429 | 7/2017 |
| WO | WO 2017/120537 | 7/2017 |
| WO | WO 2017/121877 | 7/2017 |
| WO | WO 2017/132928 | 8/2017 |
| WO | WO 2017/134051 | 8/2017 |
| WO | WO 2017/136342 | 8/2017 |
| WO | WO 2017/139468 | 8/2017 |

OTHER PUBLICATIONS

Arcila et al., "EGFR Exon 20 Insertion Mutations in Lung Adenocarcinomas: Prevalence, Molecular Heterogeneity, and Clinicopathologic Characteristics" Mol Cancer Ther. (2013) 12(2):220-229.

Ballard et al., "Preclinical Comparison of Osimertinib with Other EGFR-TKIs in EGFR-Mutant NSCLC Brain Metastases Models, and Early Evidence of Clinical Brain Metastases Activity" Clinical Cancer Research (2016) 22(20):5130-5140.

Banno et al., "Sensitivities to various epidermal growth factor receptor-tyrosine kinase inhibitors of uncommon epidermal growth factor receptor mutations L861Q and S768I: What is the optimal epidermal growth factor receptor-tyrosine kinase inhibitor?" Cancer Science (2016) 107(8):1134-1140.

Belikov et al., "Pharmaceutical Chemistry" (2007) 27-29.

(56) References Cited

OTHER PUBLICATIONS

Bernabe et al., "What do we need to make circulating tumour DNA (ctDNA) a routine diagnostic test in lung cancer?" European Journal of Cancer (2017) 81:66-73.
Bullock et al., "Lessons Learned: Dose Selection of Small Molecule-Targeted Oncology Drugs" Clinical Cancer Research (2016) 22(11):2630-2638.
CAS Reg. No. 2044704-62-1, Entered Dec. 8, 2016.
CAS Reg. No. 2044702-65-8, Entered Dec. 8, 2016.
CAS Reg. No. 2044702-55-6, Entered Dec. 8, 2016.
CAS Reg. No. 2044702-39-6, Entered Dec. 8, 2016.
CAS Reg. No. 2044702-33-0, Entered Dec. 8, 2016.
CAS Reg. No. 1956306-73-2, Entered Jul. 20, 2016.
CAS Reg. No. 1158743-04-4, Entered Jun. 17, 2009.
CAS Reg. No. 1158615-18-9, Entered Jun. 16, 2009.
CAS Reg. No. 1158558-81-6, Entered Jun. 16, 2009.
CAS Reg. No. 1158433-37-4, Entered Jun. 16, 2009.
CAS Reg. No. 1158429-55-0, Entered Jun. 16, 2009.
CAS Reg. No. 1158344-65-0, Entered Jun. 16, 2009.
CAS Reg. No. 1158333-43-7, Entered Jun. 16, 2009.
CAS Reg. No. 1158235-74-5, Entered Jun. 16, 2009.
Cecil Textbook of Medicine, 1996, Bennet & Plum (edited by), W.B. Saunders Co., pp. 1004-1010, 20th edition, vol. 1.
Chabon et al., "Circulating tumour DNA profiling reveals heterogeneity of EGFR inhibitor resistance mechanisms in lung cancer patients" Nature Communications (2016) 7:11815.
Chakrabarti et al., "Pharmacokinetics and Drug Interactions Determine Optimum Combination Strategies in Computational Models of Cancer Evolution" Cancer Research (2017) 77(14):3908-3921.
Chen et al., "Osimertinib (AZD9291) Enhanced the Efficacy of Chemotherapeutic Agents inABCB1- and ABCG2-Overexpressing Cells In Vitro, In Vivo, and Ex Vivo" Molecular Cancer Therapeutics (2016) 15(8):1845-1858.
Chuang et al., "Rociletinib, a third generation EGFR tyrosine kinase inhibitor: current data and future directions" Expert Opinion on Pharmacotherapy (2016) 17(7):989-993.
Cross et al., "AZD9291, an Irreversible EGFR TKI, Overcomes T790M-Mediated Resistance to EGFR Inhibitors in Lunch Cancer" Cancer Discovery, (2014) 4(9):1046-1061.
Day et al., "HER2 and EGFR overexpression support metastatic progression of prostate cancer to bone" Cancer Res (2017) 77(1):74-85.
Dermer, "Another Anniversary for the War on Cancer", Bio/Technology (1994) 320:12.
Dickinson et al., "Metabolic disposition of osimertinib in rats, dogs, and humans: insightsinto a drug designed to bind covalently to a cysteine residue of epidermal growth factor receptor" Drug Metabolism & Disposition (2016) 44(8):1201-1212.
Doe Be Le et al, "New Strategies to Overcome Limitations of Reversible EGFR Tyrosine Kinase Inhibitor Therapy in Non-Small Cell Lung Cancer", Lung Cancer (2010) 69:1-12.
Dong et al., "Elucidation of Resistance Mechanisms to Second-Generation ALK Inhibitors Alectinib and Ceritinib in Non-Small Cell Lung Cancer Cells" Neoplasia (New York, NY, United States) (2016) 18(3):162-171.
Ercan et al. "EGFR Mutations and Resistance to Irreversible Pyrimidine-Based EGFR Inhibitors" Clinical Cancer Research (2015) 21(17):3913-3923.
Eberlein et al., "Acquired Resistance to the Mutant-Selective EGFR Inhibitor AZD9291 Is Associated with Increased Dependence on RAS Signaling in Preclinical Models" Cancer Research (2015) 75(12):2489-2500.
Finlay et al., "Discovery of a Potent and Selective EGFR Inhibitor (AZD9291) of BothSensitizing and T790M Resistance Mutations That Spares the Wild Type Form of the Receptor" J. Med. Chem. (2014) 57(20):8249-8267.
Fresheny, Culture of Animal Cells, A Manual of Basic Techniques, 1983, Alan R. Liss, Inc., New York, p. 4.

Gao et al., "The safety and efficacy of osimertinib for the treatment of EGFR T790M mutation positive non-small-cell lung cancer" Expert Review of Anticancer Therapy (2016) 16(4):383-390.
Gao et al., "Synthesis and evaluation of osimertinib derivatives as potent EGFR inhibitors" Bioorganic & Medicinal Chemistry (2017) 25(17):4553-4559.
Gil-Bazo et al., "AZD9291 in TKI EGFR resistance in non-small cell lung cancer and the new concept of phase I trials" Translational Lung Cancer Research (2016) 5(1):85-88.
Golub et al., "Molecular Classification of Cancer: Class Discovery and Class Prediction by Gene Expression Monitoring", Science (1999) 286:531-537.
Goss et al., "Osimertinib for pretreated EGFR Thr790Met-positive advanced non-small-cell lung cancer (AURA2): a multicentre, open-label, single-arm, phase 2 study" Lancet Oncology (2016) 17(12):1643-1652.
Greig, S.L., "Osimertinib: First Global Approval" Drugs (2016) 76(2):263-273.
Ha et al., "Novel heterocycle-substituted pyrimidines as inhibitors of NF-kB transcription regulation related to TNF-a cytokine release" Bioorganic & Medicinal Chemistry Letters (2008) 18(2):653-656.
Hanan et al., 4-Aminoindazolyl-dihydrofuro[3,4-d]pyrimidines as non-covalent inhibitors of mutant epidermal growth factor receptor tyrosine kinase Bioorganic & Medicinal Chemistry Letters (2016) 26(2):534-539.
He et al., "Research progress of osimertinib in treating non-small cell lung cancer" Zhongguo Xinyao Yu Linchuang Zazhi (2016) 35(6):398-404.
Holmes et al., "Self-optimisation of the final stage in the synthesis of EGFR kinase inhibitor AZD9291 using an automated flow reactor" Reaction Chemistry & Engineering (2016) 1(4):366-371.
Hsiao et al., "Osimertinib (AZD9291) Attenuates the Function of Multidrug Resistance-Linked ATP-Binding Cassette Transporter ABCB1 in Vitro" Molecular Pharmaceutics (2016) 13(6):2117-2125.
Hughes, D.L., "Patent Review of Manufacturing Routes to Oncology Drugs: Carfilzomib,Osimertinib, and Venetoclax" Organic Process Research & Development (2016) 20(12):2028-2042.
Hwang et al., "Expression of Neuroendocrine Factor VGF in Lung Cancer Cells Confers Resistance to EGFR Kinase Inhibitors and Triggers Epithelial-to-Mesenchymal Transition" Cancer Research (2017) 77(11):3013-3026.
Ichihara et al., "SFK/FAK Signaling Attenuates Osimertinib Efficacy in Both Drug-Sensitiveand Drug-Resistant Models of EGFR-Mutant Lung Cancer" Cancer Research (2017) 77(11):2990-3000.
Jiang et al., "Clinical activity of the mutant-selective EGFR inhibitor AZD9291 in patients with EGFR inhibitor-resistant non-small cell lung cancer" Translational Lung Cancer Research (2014) 3(6):370-372.
Jorge et al., "Epidermal growth factor receptor (EGFR) mutations in lung cancer: preclinical and clinical data" Brazilian Journal of Medical and Biological Research (2014) 47(11):929-939.
Juchum et al. Drug Resistance Updates 20 (2015) 12-28.
Kato et al, "Numerical indices based on circulating tumor DNA for the evaluation of therapeutic response and disease progression in lung cancer patients" Scientific Reports (2016) 6:29093.
Kim et al., "Mechanisms of Acquired Resistance to AZD9291: A Mutation-Selective, Irreversible EGFR Inhibitor" Journal of Thoracic Oncology (2015) 10(12):1736-1744.
Kelley et al., "Erlotinib in the treatment of advanced pancreatic cancer" Biologics: Targets & Therapy (2008) 2(1):83-95.
Kobayashi et al., "Characterization of EGFR T790M, L792F, and C797S Mutations as Mechanisms of Acquired Resistance to Afatinib in Lung Cancer" Molecular Cancer Therapeutics (2017) 16(2):357-364.
Koi et al., "EGFR-amplification plus gene expression profiling predicts response to combined radiotherapy with EGFR-inhibition: A preclinical trial in 10 HNSCC-tumour-xenograft models" Radiotherapy and Oncology (2017) 124:496-503.
Ku et al., "AZD9291 overcomes T790 M-mediated resistance through degradation of EGFRL858R/T790M in non-small cell lung cancer cells" Investigational New Drugs (2016) 34(4):407-415.

(56) References Cited

OTHER PUBLICATIONS

Lampson et al., "Activity of erlotinib when dosed below the maximum tolerated dose for EGFR-mutant lung cancer: Implications for targeted therapy development" Cancer (2016) 122(22):3456-3463.
Li et al., "Novel Selective and Potent EGFR inhibitor that overcomes T790M-mediated resistance in non-small cell lung cancer" Molecules (2016) 21(11):1462/1-1462/14.
Liao et al., "Second and third-generation epidermal growth factor receptor tyrosine kinaseinhibitors in advanced nonsmall cell lung cancer" Current Opinion in Oncology (2015) 27(2):94-101.
Liu et al., "A novel and efficient synthesis of anti-cancer agent, Mereletini" Journal of Chemical Research (2015) 39(6):318-320.
Liu et al., "Mechanism and strategy of the secondary resistance to EGFR-TKI in patients with lung cancer" Guoji Zhongliuxue Zazhi (2015) 42(1), 56-59.
Lo Nigro et al., "Prognostic and predictive biomarker in metastatic colorectal cancer anti-EGFR therapy" World J. Gastroenterol (2016) 22(30):6944-6954.
Longo et al., "Bay846, a new irreversible small molecule inhibitor of EGFR and Her2, is highly effective against malignant brain tumor models" Invest New Drugs (2012) 31:2161- 2172.
Lowder et al., "Structural Differences between Wild-Type and Double Mutant EGFR Modulated by Third-Generation Kinase Inhibitors" J. Am. Chem. Soc. (2015) 137(20):6456-6459.
Meador et al., "Optimizing the Sequence of Anti-EGFR-Targeted Therapy in EGFR-Mutant Lung Cancer" Molecular Cancer Therapeutics (2015) 14(2):542-552.
Mehner et al., "Serine protease inhibitior Kazal type 1 (SPINK 1) drives proliferation and anoikis resistance in a subject of ovarian cancers" Oncotarget (2015) 6:35737-35754.
Mimeault et al., "Complex Oncogenic Signaling Networks Regulate Brain Tumor-Initiating Cells and Their Progenies: Pivotal Roles of Wild-Type EGFR, EGFRvIII Mutant and Hedgehog Cascades and Novel Multitargeted Therapies" Brain Pathologies (2011) 21:479-500.
Mitsudomi et al., "Epidermal growth factor receptor in relation to tumor development: EGFR gene and cancer" FEBS J. (2010) 277(2):301-308.
Miyamoto et al., "Recent Advances in Targeting the EGFR Signaling Pathway for the Treatment of Metastatic Colorectal Cancer" Int. J. Mol. Sci. (2017) 18:752.
Mizuuchi et al., "Oncogene swap as a novel mechanism of acquired resistance to epidermal growth factor receptor-tyrosine kinase inhibitor in lung cancer" Cancer Science (2016) 107(4):461-468.
Nanjo et al., "MET Copy Number Gain Is Associated with Gefitinib Resistance in Leptomeningeal Carcinomatosis of EGFR-mutant Lung Cancer" Molecular Cancer Therapeutics (2017) 16(3):506-515.
Neal et al., "Developing biomarker-specific end points in lung cancer clinical trials" Nature Reviews Clinical Oncology (2015) 12(3):135-146.
Noda et al., "Addressing epidermal growth factor receptor tyrosine kinase inhibitor resistance in non-small cell lung" Expert Review of Respiratory Medicine (2016) 10(5):547-556.
Oliveira-Cunha et al., "Epidermal Growth Factor Receptor in Pancreatic Cancer" Cancers (2011) 3:1513-1526.
Ortiz-Cuaran et al., "Heterogeneous Mechanisms of Primary and Acquired Resistance to Third-Generation EGFR Inhibitors" Clinical Cancer Research (2016) 22(19):4837-4847.
Oxnard et al., "Natural History and Molecular Characteristics of Lung Cancers Harboring EGFR Exon 20 Insertions" J Thorac Oncol. (2013) 8(2):179-184.
Oxnard et al., "Association between plasma genotyping and outcomes of treatment with osimertinib (AZD9291) in advanced non-small-cell lung cancer" Journal of Clinical Oncology (2016) 34(28):3375-3382.
Pao et al., "Rational, Biologically Based Treatment of EGFR-mutant Non-small-cell Lung Cancer", Nature (2010) 10:760-774.
Patel et al., "Recent updates on third generation EGFR inhibitors and emergence of fourth generation EGFR inhibitors to combat C797S resistance" European Journal of Medicinal Chemistry (2017) 142:32-47.
Pccompound-selected items-1-200 of 338 Create Date Jun. 10, 2013 to Feb. 23, 2016.
Pccompound-selected items-201-338 of 338, Create Date Feb. 23, 2016 to Apr. 9, 2016.
Peters et al., "Oral epidermal growth factor receptor tyrosine kinase inhibitors for the treatment of non-small cell lung cancer: Comparative pharmacokinetics and drug-drug interactions" Cancer Treatment Reviews (2014) 40(8):917-926.
Planchard et al., "Osimertinib Western and Asian clinical pharmacokinetics in patients and healthy volunteers: implications for formulation, dose, and dosing frequency in pivotal clinical studies" Cancer Chemotherapy and Pharmacology (2016) 77(4):767-776.
Planken et al., "Discovery of N-((3R,4R)-4-Fluoro-1-(6-((3-methoxy-1-methyl-1H-pyrazol-4-yl)amino)-9-methyl-9H-purin-2-yl)pyrrolidine-3-yl)acrylamide (PF-06747775) through Structure-Based Drug Design: A High Affinity Irreversible Inhibitor Targeting Oncogenic EGFR Mutants with Selectivity over Wild-Type EGFR" Journal of Medicinal Chemistry (2017) 60(7):3002-3019.
Politi et al. "The Next Wave of EGFR Tyrosine Kinase Inhibitors Enter the Clinic" Cancer Cell (2015), 27(6):751-753.
Presutti et al., "MET gene amplification and MET receptor activation are not sufficient to predict efficacy of combined MET and EGFR inhibitors in EGFR TKI-resistant NSCLC cells" PLoS One (2015) 10(11):e0143333/1-e0143333/22.
"Process for the preparation of N-[2-[[2-(dimethylamino)ethyl]methylamino]-4-methoxy-5-[[4-(1-methyl-1H-indol-3-yl)-2-pyrimidinyl]amino]phenyl]-2-propenamide, or a salt thereof and intermediates thereof" (2016):1-10.
Remon et al., "Beyond EGFR TKI in EGFR-mutant Non-Small Cell Lung Cancer Patients: Main Challenges Still to be Overcome", Cancer Treatment Reviews (2014) 40:723-729.
Remon et al., "AZD9291 in EGFR-mutant advanced non-small-cell lung cancer patients" Future Oncology (2015) 11(22):3069-3081.
Rho et al., "Superior Efficacy and Selectivity of Novel Small-Molecule Kinase Inhibitors of T790M-Mutant EGFR in Preclinical Models of Lung Cancer" Cancer Research (2017) 77(5):1200-1211.
Ricciuti et al., "Osimertinib (AZD9291) and CNS Response in Two Radiotherapy-Naive Patients with EGFR-Mutant and T790M-Positive Advanced Non-Small Cell Lung Cancer" Clinical Drug Investigation (2016) 36(8):683-686.
Rood et al., "Liquid chromatography-tandem mass spectrometric assay for the T790M mutant EGFR inhibitor osimertinib (AZD9291) in human plasma" Journal of Chromatography B: Analytical Technologies in the Biomedical and Life Sciences (2016) 1031:80-85.
Scartozzi et al., "Epidermal Growth Factor Receptor (EGFR) gene copy number (GCN) correlates with clinical activity of irinotecan-cetuximab in K-RAS wild-type colorectal cancer: a fluorescence in situ (FISH) and chromogenic in situ hybridization (CISH) analysis" BMC Cancer (2009) 9:303.
Shi et al., "Met gene amplification and protein hyperactivation is a mechanism of resistance to both first and third generation EGFR inhibitors in lung cancer treatment" Cancer Letters (2016) 380(2):494-504.
Singer et al., "Efficacy of Combined VEGF and EGFR Inhibition in Metastatic Papillary Renal Cell Carcinoma Associated with Hereditary Leiomyomatosis and Renal Cell Cancer" Mid-Atlantic Section of the American Urological Association Annual Meeting, Oct. 24-27, 2013, The Greenbrier, White Sulphur Springs, WV (Abstract).
Smith et al., "Characterization of Covalent-Reversible EGFR Inhibitors" ACS Omega (2017) 2(4):1563-1575.
Soejima et al., "Osimertinib for EGFR T790M mutation-positive non-small cell lung cancer" Expert Review of Clinical Pharmacology (2017) 10(1):31-38.
Song et al., "Synthesis and biological evaluation of azole-diphenylpyrimidine derivatives (AzDPPYs) as potent T790M mutant form of epidermal growth factor receptor inhibitors" Bioorganic & Medicinal Chemistry (2016) 24(21):5505-5512.
Stinchcombe, T.E., "Recent advances in the treatment of non-small cell and small cell lung cancer" F1000Prime Reports (2014) 6, 1-8.

(56) References Cited

OTHER PUBLICATIONS

Stinchcombe, T.E., "AZD9291 in epidermal growth factor receptor inhibitor-resistant non-small-cell lung cancer" Translational Lung Cancer Research (2016) 5(1):92-94.
Steuer et al., "The next generation of epidermal growth factor receptor tyrosine kinase inhibitors in the treatment of lung cancer" Cancer (2015), 121(8):E1-E6.
Sun, Y., "An overview of new drugs approved in the US, EU and Japan in Apr. 2016" Yaoxue Jinzhan (2016), 40(5):395-400.
Tan et al., "Treatment approaches for EGFR-inhibitor-resistant patients with non-small-cell lung cancer" Lancet Oncology (2015), 16(9), e447-e459.
Tang et al., "Osimertinib induces autophagy and apoptosis via reactive oxygen species generation in non-small cell lung cancer cells" Toxicology and Applied Pharmacology (2017) 321:18-26.
"Targeting Resistance in Lung Cancer" Cancer Discovery (2013) 3(12), OF9/1-OF9/2.
Taylor et al., "Enhanced MAPK signaling drives ETS1-mediated induction of miR-29b leading to downregulation of TET1 and changes in epigenetic modifications in a subset of lung SCC" Oncogene (2016) 35:4345-4357.
Thress et al., "Acquired EGFR C797S mutation mediates resistance to AZD9291 in non-small cell lung cancer harboring EGFR T790M" Nature Medicine (2015) 21(6):560-562.
Tomassi et al., "Indazole-Based Covalent Inhibitors To Target Drug-Resistant Epidermal Growth Factor Receptor" Journal of Medicinal Chemistry (2017) 60(6):2361-2372.
Uchibori et al., "Brigatinib combined with anti-EGFR antibody overcomes osimertinib resistance in EGFR-mutated non-small-cell lung cancer" Nature Communications (2017) 8:14768.
Villadolid et al., "Management of hyperglycemia from epidermal growth factor receptor (EGFR) tyrosine kinase inhibitors (TKIs) targeting T790M-mediated resistance" Translational Lung Cancer Research (2015) 4(5):576-583.
Wang et al., "Third-generation inhibitors targeting EGFR T790M mutation in advanced non- small cell lung cancer" Journal of Hematology & Oncology (2016) 9:34/1-34/7.
Wang et al., "EAI045: The fourth-generation EGFR inhibitor overcoming T790M and C797S resistance" Cancer Letters (2017) 385:51-54.
Xu et al., "AC0010, an irreversible EGFR inhibitor selectively targeting mutated EGFR andovercoming T790M-induced resistance in animal models and lung cancer patients" Molecular Cancer Therapeutics (2016) 15(11):2586-2597.
Yang et al., "Afatinib versus cisplatin-based chemotherapy for EGFR mutation-positive lung adenocarcinoma (LUX-Lung 3 and LUX-Lung 6): analysis of overall survival data from two randomised, phase 3 trials" Lancet Oncology (2015) 16(2):141-151.
Yap et al., "Continuing EGFR inhibition beyond progression in advanced non-small cell lung cancer" European Journal of Cancer (2017) 70:12-21.
Yates et al., "Irreversible Inhibition of EGFR: Modeling the Combined Pharmacokinetic-Pharmacodynamic Relationship of Osimertinib and Its Active Metabolite AZ5104" Molecular Cancer Therapeutics (2016) 15(10):2378-2387.
Ye et al., "Targeting FBW7 as a Strategy to Overcome Resistance to Targeted Therapy in Non-Small Cell Lung Cancer" Cancer Research (2017) 77(13):3527-3539.
Yosaatmadja et al., "Binding mode of the breakthrough inhibitor AZD9291 to epidermal growth factor receptor revealed" Journal of Structural Biology (2015) 192(3):539-544.
Yu et al., "A structure-guided optimization of pyrido[2,3-d]pyrimidin-7-ones as selective inhibitors of EGFRL858R/T790M mutant with improved pharmacokinetic properties" European Journal of Medicinal Chemistry (2017) 126: 1107-1117.
Zhang et al., "Progress in pharmacokinetic studies of tyrosine kinase Inhibitors" Zhongguo Xinyao Zazhi (2016) 25(14):1600-1607.

Zhang et al., "Osimertinib (AZD9291), a mutant-selective EGFR inhibitor, reverses ABCB1-mediated drug resistance in cancer cells" Molecules (2016) 21(9):1236/1-1236/15.
Zhang et al., "Design, synthesis, SAR discussion, in vitro and in vivo evaluation of novel selective EGFR modulator to inhibit L858R/T790M double mutants" European Journal of Medicinal Chemistry (2017) 135:12-23.
Zhao et al., "Delineation of Polypharmacology across the Human Structural Kinome Using aFunctional Site Interaction Fingerprint Approach" Journal of Medicinal Chemistry (2016) 59(9):4326-4341.
Zheng et al., "Combined Erlotinib and PF-03084014 treatment contributes to synthetic lethality in head and neck squamous cell carcinoma" Col Prolif (2018) 51(3):e12424 (Abstract).
Zhu et al., "Advance in development of the drugs targeting EGFR for cancer therapy" Zhongguo Xinyao Zazhi (2015) 24(20):2376-2382.
Zhu et al., "New and Convergent Synthesis of Osimertinib" Journal of Heterocyclic Chemistry (2017) 54:2898-2901.
Search Report and Written Opinion mailed Jul. 24, 2017 for PCT Application No. PCT/US2017/034163, filed May 24, 2017.
International Preliminary Report on Patentability issued Nov. 27, 2018 for PCT Application No. PCT/US2017/034163, filed May 24, 2017.
First Examination Report dated Aug. 30, 2019 for New Zealand Application No. 747854, filed May 24, 2017.
Extended European Search Report dated Oct. 2, 2019 for EP Application No. 17803481.5, filed May 24, 2017.
Office Action Jul. 6, 2018 for U.S. Appl. No. 15/603,789, filed May 24, 2017.
Office Action Apr. 27, 2020 for Chinese Application No. 201780032202.6, filed May 24, 2017.
Office Action dated Jun. 26, 2020 for Russian Application No. 2018138584, filed May 24, 2017.
Written Opinion dated Feb. 11, 2020 for SG Application No. 11201809751X, filed May 24, 2017.
Examination Report dated Jun. 8, 2020 for New Zealand Application No. 747854, filed May 24, 2017.
Written Opinion dated Jul. 13, 2020 for SG Application No. 11201809751X, filed May 24, 2017.
Office Action dated Jul. 29, 2020 for Israeli Application No. 263081, filed May 24, 2017.
Office Action Oct. 21, 2020 for Chinese Application No. 201780032202.6, filed May 24, 2017.
Examination Report dated Oct. 9, 2020 for New Australian Application No. 2017269335, filed May 24, 2017.
Office Action dated Sep. 2, 2020 for Mexican Application No. MX/a/2018/013413, filed May 24, 2017.
First Examination Report dated Nov. 25, 2020 for Indian Application No. 747854, filed May 24, 2017.
Office Action dated Dec. 11, 2020 for Russian Application No. 2018138584, filed May 24, 2017.
Office Action dated Feb. 16, 2021 for Mexican Application No. MX/a/2018/013413, filed May 24, 2017.
Examination Report dated Jan. 21, 2021 for SG Application No. 11201809751X, filed May 24, 2017.
Office Action drafted Mar. 17, 2021 for Japanese Application No. 2018-561695, filed May 24, 2017.
Office Action dated Apr. 7, 2021 for Chinese Application No. 201780032202.6, filed May 24, 2017.
Communication dated Feb. 28, 2022 for EP Application No. 17803481.5, filed May 24, 2017.
Office Action dated Feb. 9, 2022 for Mexican Application No. MX/a/2021/007773, filed May 24, 2017.
Examination Report dated Nov. 29, 2022 for Australian Application No. 2021240162, filed May 24, 2017.
Office Action dated Nov. 17, 2021 for Brazilian Application No. BR112018074232-5, filed May 24, 2017.
Office Action dated Jul. 27, 2023 for Canadian Patent Application No. 3023176, filed May 24, 2017.
Hearing Notice dated Oct. 8, 2022 for Indian Application No. 747854, filed May 24, 2017.

(56) References Cited

OTHER PUBLICATIONS

Office Action dated Mar. 28, 2023 for KR Patent Application No. 10-2022-7031434, filed May 24, 2017.
Office Action dated Jun. 28, 2022 for Mexican Application No. MX/a/2021/007773, filed May 24, 2017.
Office Action dated Sep. 15, 2022 for Mexican Application No. MX/a/2021/007773, filed May 24, 2017.
Office Action and Search Report dated Jun. 24, 2021 for Taiwanese Application No. 106117475, filed May 25, 2017.
Office Action dated Jan. 11, 2022 for Korean Patent Application No. 10-2018-7034187, filed May 24, 2017.
Office Action dated Nov. 28, 2023 for Brazilian Application No. BR112018074232-5, filed May 24, 2017.

EGFR INHIBITOR COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. application Ser. No. 16/703,544, filed Dec. 4, 2019, Ser. No. 15/603,789, filed May 24, 2017, and U.S. Provisional Application No. 62/342,141, filed May 26, 2016. The present application is a continuation of U.S. application Ser. No. 16/703,544, filed Dec. 4, 2019, which is a divisional of U.S. application Ser. No. 15/603,789, filed May 24, 2017, and claims priority to U.S. Provisional Application No. 62/342,141, filed May 26, 2016.

BACKGROUND

Field

The present application relates to the fields of chemistry, biochemistry and medicine. More particularly, disclosed herein are EGFR inhibitor compounds, together with pharmaceutical compositions, and methods of synthesizing the same. Also disclosed herein are methods of ameliorating and/or treating a cancer with one or more of the compounds described herein.

Description

Overexpression of the EGFR gene has been identified in a variety of cancers including head and neck, brain, breast, colon and lung. In addition to overexpression, EGFR activating mutations have been detected in a subset of non-small cell lung cancers (NSCLCs) tumors. The majority of patients who respond well to first and second-generation EGFR inhibitors eventually develop resistance to these inhibitors. The most common resistance mechanism is an acquired gatekeeper mutation of threonine-to-methionine (T790M) in the EGFR gene. EGFR overexpression or activation, and acquired EGFR T790M mutation is observed in human cancers and is associated with high rates of cancer cell proliferation and drug resistance.

SUMMARY

Some embodiments disclosed herein relate to a compound of Formula (I), or a pharmaceutically acceptable salt thereof.

Some embodiments described herein relate to a pharmaceutical composition, that can include an effective amount a compound of Formula (I), or a pharmaceutically acceptable salt thereof.

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein that can include contacting a malignant growth or a tumor, wherein the malignant growth or tumor is due to a cancer described herein.

Some embodiments described herein relate to a method for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated) that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a sample that includes a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated).

Some embodiments described herein relate to a method for ameliorating or treating a cancer described herein that can include inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated) using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein by inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein by inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated).

DETAILED DESCRIPTION

Inhibition of EGFR can have therapeutic effects in the treatment of cancer. It has been shown that EGFR can mutate and become activated, driving tumor growth. Epidermal growth factor receptor (EGFR) has an extracellular ligand binding domain, a transmembrane portion and intracellular tyrosine kinase and regulatory domains. Upon binding of a specific ligand, EGFR undergoes conformational change and phosphorylation of the intracellular domain occurs leading to downstream signal transduction that regulates cellular proliferation. Constitutive activation of EGFR leads to increased intracellular pathways activity which eventually leads to cell proliferation, angiogenesis, invasion and/or metastasis.

Overexpression of the EGFR gene has been identified in a variety of cancers including head and neck, brain, breast, colon and lung. In non-small cell lung cancer, the frequency of EGFR overexpression has been determined to be 40% to 80%. In addition to overexpression, EGFR activating mutations have been detected in a subset of non-small cell lung cancers (NSCLCs) tumors, which represent 10% to 30% of all NSCLCs. The mutations occur in exons 18, 19, 20 and 21 of the tyrosine kinase domain of the EGFR gene. The majority of mutations in exon 21 are point mutations whereas exon 19 consists of almost entirely in-frame deletions. The L858R point mutation and the deletion in exon 19 (such as delA740-A750), account up to 86% of all EGFR mutations. Also, EGFR exon 20 insertions comprise approximately 4-9.2% of all EGFR-mutated lung tumors (Arcila et al., Mol Cancer Ther. (2013) 12(2):220-229; Mitsudomi et al., FEBS J. (2010) 277(2):301-308; and Oxnard et al., J Thorac Oncol. (2013) 8(2):179-184). These mutations result in increased kinase activity of the EGF receptor in the absence of growth factors. The above-mentioned mutations in EGF receptor were shown to be a predictive biomarker of efficacy in response to EGFR tyrosine kinase inhibitors. These findings have revolutionized the way in which EGFR inhibitors are used as therapy for NSCLC patients with activating EGFR mutations. The EGFR inhibitors, erlotinib and gefitinib (considered first generation EGFR inhibitors) were approved in the United States, initially as second-line therapies. However, subsequent clinical trials of EGFR inhibitors, including the first-generation EGFR inhibitors (gefitinib) and second-generation EGFR inhibitor (afatinib) demonstrated significant improvements in overall response rates in NSCLC patients with EGFR activating mutations in the frontline setting.

However, the majority of patients who respond well to the first and second-generation EGFR inhibitors eventually develop resistance to these inhibitors. The most common resistance mechanism, which is observed in approximately 50% of the patients, is an acquired gatekeeper mutation of threonine-to-methionine (T790M) in the EGFR gene. This mutation increases the receptor's affinity for ATP and decreases the effectiveness of first generation EGFR inhibitors. Therefore, the NSCLC patients who refract on first and second-generation EGFR inhibitors need new therapies that can overcome the acquired resistance associated with the T790M mutation.

Provided herein are compounds that can inhibit the kinase activity of EGFR. As EGFR inhibitors, the compounds described herein can be used to ameliorate and/or treat a variety of cancers (including those with acquired EGFR T790M mutation, a mutation at L858R, a deletion in exon 19 (such as A740-A750), inhibiting the activity of EGFR with an insertion in exon 20, inhibiting the activity of wildtype EGFR and/or where EGFR is overexpressed or activated) such as non-small cell lung, head and neck, brain, breast and colon cancer.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from D (deuterium), halogen, hydroxy, $C_{1-4}$ alkoxy, $C_{1-4}$ alkyl, $C_{3-8}$ cycloalkyl, aryl, heteroaryl, $C_{1-6}$ haloalkyl, cyano, alkenyl, alkynyl, cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amine group and a di-substituted amine group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3—$, $CH_3CH_2—$, $CH_3CH_2CH_2—$, $(CH_3)_2CH—$, $CH_3CH_2CH_2CH_2—$, $CH_3CH_2CH(CH_3)—$ and $(CH_3)_3C—$. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded, either indirectly through intermediate atoms, or directly to one another, to form a ring, for example:

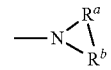

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical containing one or more carbon double bonds. The alkenyl group may have 2 to 30 carbon atoms, 2 to 12 carbon atoms or 2 to 6 carbon atoms. Examples of an alkenyl include, but are not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical containing one or more carbon triple bonds. The alkynyl group may have 2 to 30 carbon atoms, 2 to 12 carbon atoms or 2 to 6 carbon atoms. Examples of an alkenyl include, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted.

As used herein, the term "fused" refers to a connectivity between two rings in which two adjacent atoms sharing at least one bond (saturated or unsaturated) are common to the rings. For example, in the following structure, rings A and B are fused

Examples of fused ring structures include, but are not limited to, decahydronaphthalene, 1H-indole, quinolone, chromane, bicyclo[2.1.0]pentane and 6,7,8,9-tetrahydro-5H-benzo[7]annulene.

As used herein, the term "bridged" refers to a connectivity wherein three or more atoms are shared between two rings. The following structures and

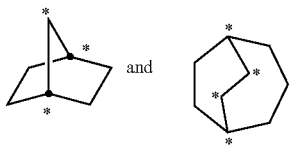 [SMILES: C1C[C@H]2CC[C@H]1C2 ; C1CC2CCC(C1)CC2]

are examples of "bridged" rings because the indicated atoms are shared between at least two rings. Examples of bridged ring structures include, but are not limited to, bicyclo[1.1.1]pentane, 2-oxabicyclo[1.1.1]pentane, 5-azabicyclo[2.1.1]hexane, 6-azabicyclo[3.1.1]heptane, adamantane and norbornane.

As used herein, the term "spiro" refers to a connectivity between two rings wherein the rings have only one atom in common. For example, in the structure

rings C and D are joined by a spiro connection. Examples of spiro connected ring structures include, but are not limited to, spiro[3.3]heptane, 2,6-diazaspiro[3.3]heptane, 2-oxa-6-azaspiro[3.3]heptane, spiro[4.5]decane and 2,6-dioxaspiro[3.3]heptane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 8 to 30 atoms in the ring(s), 8 to 20 atoms in the ring(s) or 8 to 10 atoms in the ring(s). When composed of two or more rings, the rings may be joined together in a fused, bridged or spiro fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1, 2, 3, 4 or 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged, or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include, but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of bridged heterocyclic compounds include, but are not limited to, 1,4-diazabicyclo[2.2.2]octane and 1,4-diazabicyclo[3.1.1]heptane. Examples of spiro-connected heterocyclic compounds include, but are not limited to, 2-azaspiro[3.3]heptane, 2,6-diazaspiro[3.3]heptane, and 2-oxa-6-azaspiro[3.3]heptane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl, and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group and/or by substituting both hydrogens on the same carbon with a cycloalkyl group

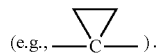

As used herein, the term "hydroxy" refers to a —OH group.

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys is methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N ($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N ($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N ($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "C-thioamido" group refers to a "—C(=S)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-thioamido may be substituted or unsubstituted.

An "N-thioamido" group refers to a "RC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thioamido may be substituted or unsubstituted.

An "S-sulfonamido" group refers to a "—$SO_2$N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "R$SO_2$N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, an alkoxy, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

An "oxo" group refers to a "=O" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —$NH_2$ group.

A "mono-substituted amine" group refers to a "—NHR" group in which R can be an alkyl, an alkenyl, an alkynyl, a haloalkyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amine" group refers to a "—$NR_AR_B$" group in which $R_A$ and $R_B$ can be independently an alkyl, an alkenyl, an alkynyl, a haloalkyl, a cycloalkyl, a cycloalkenyl, aryl, heteroaryl, heterocyclyl, cycloalkyl(alkyl), aryl (alkyl), heteroaryl(alkyl) or heterocyclyl(alkyl), as defined herein. A di-substituted amino may be substituted or unsubstituted. Examples of di-substituted amino groups include, but are not limited to, —$N(methyl)_2$, —N(phenyl)(methyl), —N(ethyl)(methyl) and the like.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, trifluoroacetic, benzoic, salicylic, 2-oxopentanedioic, or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine. For compounds of Formula (I), those skilled in the art understand that when a salt is formed by protonation of a nitrogen-based group (for example, $NH_2$), the nitrogen-based group can be associated with a positive charge (for example, $NH_2$ can become $NH_3^+$) and the positive charge can be balanced by a negatively charged counterion (such as $Cl^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

It is understood that, in any compound described, all tautomeric forms are also intended to be included. For example, the following are tautomers:

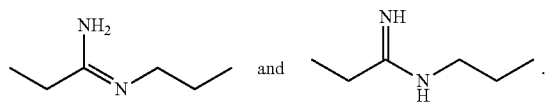

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

Compounds

Some embodiments described herein generally relate to a compound of Formula (I), or a pharmaceutically acceptable salt thereof, wherein Formula (I) has the structure:

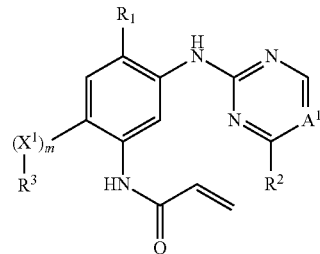

$R^1$ can be selected from hydrogen, halogen, hydroxy, cyano, an optionally substituted $C_{1-4}$ alkyl, an optionally substituted $C_{1-4}$ haloalkyl, an optionally substituted $C_{1-4}$ alkoxy and an optionally substituted $C_{1-4}$ haloalkoxy; $R^2$ can be an optionally substituted 6-15 membered heteroaryl or an optionally substituted 6-15 membered heterocyclyl, wherein the heteroaryl and the heterocyclyl independently can contains 1-4 heteroatoms selected from N, O and S; $R^3$ can be selected from hydrogen, halogen, an optionally substituted $C_{1-4}$ alkyl, an optionally substituted $C_{3-8}$ cycloalkyl, an optionally substituted aryl, an optionally substituted heteroaryl and an optionally substituted heterocyclyl, wherein when substituted, $R^3$ can be substituted by one or more substituents selected from halogen, cyano, an unsubstituted $C_{1-4}$ alkyl, an optionally substituted aryl, —C(O)$R^{5A}$, —SO$_2R^{5B}$, —NHC(O)$R^{5C}$ and —(CR$^{6A}R^{6B}$)$_n$NR$^{7A}R^{7B}$; X can be O (oxygen), S (sulfur) or NR$^4$; $R^4$ can be selected from hydrogen, an optionally substituted $C_{1-4}$ alkyl, an optionally substituted $C_{1-4}$ haloalkyl and an optionally substituted $C_{3-8}$ cycloalkyl; $R^{5A}$, $R^{5B}$ and $R^{5C}$ can be independently selected from hydrogen, an optionally substituted $C_{1-4}$ alkyl, an optionally substituted $C_{1-4}$ haloalkyl, an optionally substituted $C_{3-8}$ cycloalkyl, an optionally substituted aryl, an optionally substituted heteroaryl and an optionally substituted heterocyclyl; $R^{6A}$ and $R^{6B}$ can be independently selected from hydrogen, halogen, an optionally substituted $C_{1-4}$ alkyl, an optionally substituted $C_{1-4}$ haloalkyl and an optionally substituted $C_{3-8}$ cycloalkyl; $R^{7A}$ and $R^{7B}$ can be independently selected from hydrogen, an optionally substituted $C_{1-4}$ alkyl, an optionally substituted $C_{1-4}$ haloalkyl and an optionally substituted $C_{3-8}$ cycloalkyl; $A^1$ can be N (nitrogen) or CR$^8$; $R^8$ can be selected from hydrogen, halogen, cyano, an optionally substituted $C_{1-4}$ alkyl, an optionally substituted $C_{1-4}$ haloalkyl and an optionally substituted $C_{3-8}$ cycloalkyl; m can be 0 or 1; and n can be 0, 1, 2 or 3.

In some embodiments, $R^2$ can be an optionally substituted 6-15 membered heteroaryl. In other embodiments, $R^2$ can be an optionally substituted 6-15 membered heterocyclyl. A variety of heteroatoms can be present in one or more rings of the optionally substituted 6-15 membered heteroaryl and/or the optionally substituted 6-15 membered heterocyclyl. The number of heteroatoms can also vary. In some embodiments, 1 heteroatom can be present in one or more rings of the optionally substituted 6-15 membered heteroaryl and/or the optionally substituted 6-15 membered heterocyclyl. In other embodiments, 2 heteroatoms can be present in one or more rings of the optionally substituted 6-15 membered heteroaryl and/or the optionally substituted 6-15 membered heterocyclyl. In still other embodiments, 3 heteroatoms can be present in one or more rings of the optionally substituted 6-15 membered heteroaryl and/or the optionally substituted 6-15 membered heterocyclyl. In yet still other embodiments, 4 heteroatoms can be present in one or more rings of the optionally substituted 6-15 membered heteroaryl and/or the optionally substituted 6-15 membered heterocyclyl. In some embodiments, the heteroatom(s) can be independently selected from N (nitrogen), O (oxygen) and S (sulfur).

The number of rings in the 6-15 membered heteroaryl and/or the optionally substituted 6-15 membered heterocyclyl can vary. In some embodiments, the 6-15 membered heteroaryl and/or the optionally substituted 6-15 membered heterocyclyl can be monocyclic. In other embodiments, the 6-15 membered heteroaryl and/or the optionally substituted 6-15 membered heterocyclyl can be bicyclic. In some embodiments, $R^2$ can be an optionally substituted 5 or 6 membered monocyclic heteroaryl. In other embodiments, $R^2$ can be an optionally substituted 9 or 10 membered bicyclic heteroaryl. In still other embodiments, $R^2$ can be an optionally substituted 5 or 6 membered monocyclic heterocyclyl. In yet still other embodiments, $R^2$ can be an optionally substituted 9 or 10 membered bicyclic heterocyclyl.

In some embodiments, $R^2$ can be an optionally substituted indolyl. In other embodiments, $R^2$ can be an optionally substituted indazolyl. In still other embodiments, $R^2$ can be an optionally substituted 4,5,6,7-tetrahydroindazolyl. In yet still other embodiments, $R^2$ can be an optionally substituted

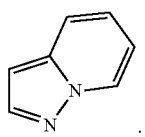

In some embodiments, $R^2$ can be an optionally substituted

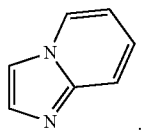

The optionally substituted indolyl, optionally substituted indazolyl, optionally substituted 4,5,6,7-tetrahydroindazolyl, optionally substituted

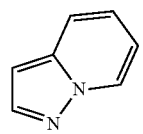

and optionally substituted

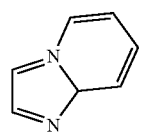

can be attached to

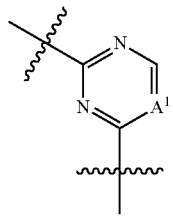

of Formula (I) at any suitable position. In some embodiments, $R^2$ can be connected to

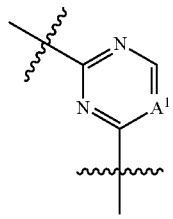

via a carbon atom. In some embodiments, $R^2$ can be an optionally substituted

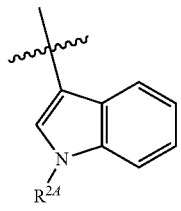

an optionally substituted

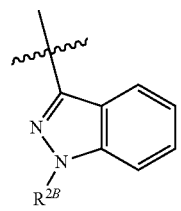

an optionally substituted

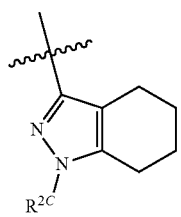

an optionally substituted

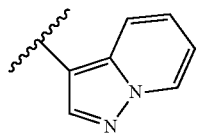

or an optionally substituted

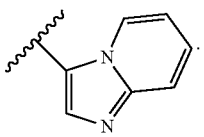 [SMILES: *c1cnc2ccccn12]

In some embodiments, $R^{2A}$, $R^{2B}$ and $R^{2C}$ can be independently, halogen, cyano, an optionally substituted $C_{1-4}$ alkyl, an optionally substituted $C_{1-4}$ haloalkyl, an optionally substituted $C_{1-4}$ alkoxy, an optionally substituted $C_{3-8}$ cycloalkyl, an unsubstituted mono-substituted amine and an unsubstituted di-substituted amine. In some embodiments, $R^{2A}$, $R^{2B}$ and/or $R^{2C}$ can be substituted by an optionally substituted $C_{3-8}$ cycloalkyl, for example, an optionally substituted bicyclo[1.1.1]pentyl. When $R^{2A}$, $R^{2B}$ and/or $R^{2C}$ is substituted, possible substituents include, but are not limited to, halogen (such as fluoro and/or chloro), cyano and an optionally substituted $C_{1-4}$ alkyl (for example, a substituted or unsubstituted methyl, a substituted or unsubstituted ethyl, a substituted or unsubstituted n-propyl, a substituted or unsubstituted iso-propyl, a substituted or unsubstituted n-butyl, a substituted or unsubstituted iso-butyl or a substituted or unsubstituted tert-butyl).

Various substituents can be present when $R^2$ is substituted, and the number of substituents can also vary. In some embodiments, when $R^2$ is substituted, $R^2$ can be substituted by one or more substituents selected from halogen, cyano, an optionally substituted $C_{1-4}$ alkyl, an optionally substituted $C_{1-4}$ haloalkyl, an optionally substituted $C_{1-4}$ alkoxy, an optionally substituted $C_{3-8}$ cycloalkyl, an unsubstituted mono-substituted amine and an unsubstituted di-substituted amine. In some embodiments, $R^2$ can be substituted by an optionally substituted $C_{3-8}$ cycloalkyl. For example, $R^2$ can be an optionally substituted bicyclo[1.1.1]pentyl. In some embodiments, $R^2$ can be an unsubstituted bicyclo[1.1.1]pentyl. In other embodiments, $R^2$ can be a substituted bicyclo[1.1.1]pentyl. Examples of substituted bicyclo[1.1.1]pentyl moieties include fluoro-substituted bicyclo[1.1.1]pentyl, chloro-substituted bicyclo[1.1.1]pentyl and cyano-substituted bicyclo[1.1.1]pentyl. In some embodiments, $R^2$ can be substituted by an optionally substituted $C_{1-4}$ alkyl. As an example, $R^2$ can be substituted by an unsubstituted $C_{1-4}$ alkyl. Examples of $C_{1-4}$ alkyls include methyl, ethyl, n-propyl, iso-propyl, n-butyl, iso-butyl and tert-butyl.

In some embodiments, m can be 0 such that $R^3$ is directly bonded to the phenyl ring shown in Formula (I). In other embodiments, m can be 1 and $R^3$ can be connected to the phenyl ring shown in Formula (I) through $X^1$. In some embodiments, $X^1$ can be O (oxygen). In other embodiments, $X^1$ can be S (sulfur). In still other embodiments, $X^1$ can be —NH. In yet still other embodiments, $X^1$ can be —N(an optionally substituted $C_{1-4}$ alkyl). In some embodiments, $X^1$ can be —N(an unsubstituted $C_{1-4}$ alkyl). As an example, $X^1$ can be —N(CH$_3$). In some embodiments, $X^1$ can be —N(an optionally substituted $C_{1-4}$ haloalkyl). In some embodiments, $X^1$ can be —N(an unsubstituted $C_{1-4}$ haloalkyl), such as N(CF$_3$). In other embodiments, $X^1$ can be —N(an optionally substituted $C_{3-8}$ cycloalkyl). In some embodiments, $X^1$ can be —N(an unsubstituted $C_{3-8}$ cycloalkyl).

In some embodiments, $R^3$ can be a substituted $C_{1-4}$ alkyl. In other embodiments, $R^3$ can be an unsubstituted $C_{1-4}$ alkyl. Examples of suitable optionally substituted $C_{1-4}$ alkyls are described herein. In some embodiments, $R^3$ can be a substituted $C_{3-8}$ cycloalkyl. In other embodiments, $R^3$ can be an unsubstituted $C_{3-8}$ cycloalkyl. As a non-limiting example, $R^3$ can be an optionally substituted $C_5$ cycloalkyl, such as an optionally substituted bicyclo[1.1.1]pentyl. In some embodiments, $R^3$ can be a substituted aryl, such as a substituted phenyl. In other embodiments, $R^3$ can be an unsubstituted aryl, for example, an unsubstituted phenyl. In some embodiments, $R^3$ can be a substituted heteroaryl. In other embodiments, $R^3$ can be an unsubstituted heteroaryl. In some embodiments, $R^3$ can be a substituted heterocyclyl. In other embodiments, $R^3$ can be an unsubstituted heterocyclyl.

When $R^3$ is an optionally substituted heteroaryl or an optionally substituted heterocyclyl, the heteroaryl and/or heterocyclyl can be monocyclic or bicyclic. For example, the optionally substituted heteroaryl and/or the an optionally substituted heterocyclyl can be an optionally substituted 4-membered monocyclic heteroaryl, an optionally substituted 4-membered monocyclic heterocyclyl, an optionally substituted 5-membered monocyclic heteroaryl, an optionally substituted 5-membered monocyclic heterocyclyl, an optionally substituted 6-membered monocyclic heteroaryl, an optionally substituted 6-membered monocyclic heterocyclyl, an optionally substituted 9-membered bicyclic heteroaryl, an optionally substituted 9-membered bicyclic heterocyclyl, an optionally substituted 10-membered bicyclic heteroaryl or an optionally substituted 10-membered bicyclic heterocyclyl.

As described herein, a heteroaryl and/or a heterocyclyl can include one or more heteroatoms in the ring(s) of the heteroaryl and/or the heterocyclyl. In some embodiments, $R^3$ can be an optionally substituted heteroaryl containing 1 heteroatom. In other embodiments, $R^3$ can be an optionally substituted heterocyclyl containing 1 heteroatom. In still other embodiments, $R^3$ can be an optionally substituted heteroaryl containing 2 heteroatoms. In yet still other embodiments, $R^3$ can be an optionally substituted heterocyclyl containing 2 heteroatoms. In some embodiments, $R^3$ can be an optionally substituted heteroaryl containing 3 or more heteroatoms. In other embodiments, $R^3$ can be an optionally substituted heterocyclyl containing 3 or more heteroatoms. Various heteroatoms can be present in the optionally substituted heteroaryl and/or the an optionally substituted heterocyclyl of $R^3$. Examples of suitable heteroatoms include N (nitrogen), O (oxygen) and S (sulfur).

In some embodiments, $R^3$ can be an optionally substituted 4-membered nitrogen-containing heterocyclyl. In other embodiments, $R^3$ can be an optionally substituted 5-membered nitrogen-containing heterocyclyl. In still other embodiments, $R^3$ can be an optionally substituted 6-membered nitrogen-containing heterocyclyl. The following are examples of suitable nitrogen containing monocyclic heterocyclyls: an optionally substituted azetidinyl, an optionally substituted pyrrolidinyl and an optionally substituted piperazinyl.

The optionally substituted heteroaryl and/or the optionally substituted heterocyclyl can be connected to $X^1$ or the shown phenyl ring of Formula (I) at any suitable position. In some embodiments, the optionally substituted heteroaryl and/or the optionally substituted heterocyclyl can be connected to $X^1$ or the shown phenyl ring of Formula (I) via a carbon. In other embodiments, the optionally substituted heteroaryl and/or the optionally substituted heterocyclyl can be connected to $X^1$ or the shown phenyl ring of Formula (I) via a nitrogen. In some embodiments, $R^3$ can be one of the following, wherein any of the moieties shown can be optionally substituted:

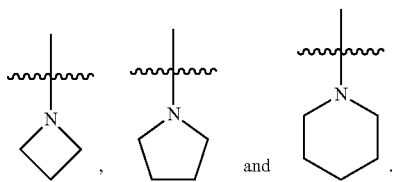

When $R^3$ is substituted, a variety and number of substituents can be present. In some embodiments, $R^3$ can be substituted with 1 substituent. In other embodiments, $R^3$ can be substituted with 2 substituents. In still other embodiments, $R^3$ can be substituted with 3 or more substituents. When more than 1 substituent is present on $R^3$, the substituent(s) can be the same as another substituent(s) or different from another substituent(s).

In some embodiments, $R^3$ can be substituted by halogen, such as fluoro and/or chloro. In some embodiments, $R^3$ can be substituted by cyano. In some embodiments, $R^3$ can be substituted by an unsubstituted $C_{1-4}$ alkyl. Examples of unsubstituted $C_{1-4}$ alkyls include methyl, ethyl, n-propyl, iso-propyl, n-butyl, iso-butyl and tert-butyl. In some embodiments, $R^3$ can be substituted by an optionally substituted aryl, such as an optionally substituted phenyl and/or an optionally substituted naphthyl.

In some embodiments, $R^3$ can be substituted by an optionally substituted acyl. The optionally substituted acyl can have the formula —C(O)$R^{5A}$, wherein $R^{5A}$ can be hydrogen, an optionally substituted $C_{1-4}$ alkyl, an optionally substituted $C_{1-4}$ haloalkyl, an optionally substituted $C_{3-8}$ cycloalkyl, an optionally substituted aryl, an optionally substituted heteroaryl or an optionally substituted heterocyclyl. In some embodiments, $R^3$ can be substituted by C(O)-(an optionally substituted $C_{1-4}$ alkyl). Suitable optionally substituted $C_{1-4}$ alkyls are described herein. In some embodiments, $R^{5A}$ can be an unsubstituted $C_{1-4}$ alkyl. When $R^{5A}$ is an unsubstituted $C_{1-4}$ alkyl, an example of acyl group that can be substituted on $R^3$ is —C(O)CH$_3$. In other embodiments, $R^{5A}$ can be a substituted $C_{1-4}$ alkyl. For example, $R^{5A}$ can be $C_{1-4}$ alkyl substituted by a mono-alkyl substituted amine and/or a di-alkyl substituted amine. In some embodiments, $R^3$ can be substituted by —C(O)CH$_2$N(CH$_3$)$_2$.

In some embodiments, $R^3$ can be substituted by an optionally substituted $C_{1-4}$ alkyl that can be substituted with a mono-alkyl substituted amine and/or a di-alkyl substituted amine. The alkyl group(s) that can be present on a mono-alkyl substituted amine and/or a di-alkyl substituted amine include an unsubstituted $C_{1-4}$ alkyl. In some embodiments, the optionally substituted $C_{1-4}$ alkyl that is substituted with a di-alkyl substituted amine can have the structure —(CH$_2$)$_2$N(CH$_3$)$_2$.

In some embodiments, $R^3$ can be substituted by —SO$_2$$R^{5B}$, wherein $R^{5B}$ can be selected from hydrogen, an optionally substituted $C_{1-4}$ alkyl, an optionally substituted $C_{1-4}$ haloalkyl, an optionally substituted $C_{3-8}$ cycloalkyl, an optionally substituted aryl, an optionally substituted heteroaryl and an optionally substituted heterocyclyl. In some embodiments, $R^3$ can be substituted by —NHC(O)$R^{5C}$, wherein $R^{5C}$ can be selected from hydrogen, an optionally substituted $C_{1-4}$ alkyl, an optionally substituted $C_{1-4}$ haloalkyl, an optionally substituted $C_{3-8}$ cycloalkyl, an optionally substituted aryl, an optionally substituted heteroaryl and an optionally substituted heterocyclyl.

In some embodiments, $R^3$ can be substituted by —(C$R^{6A}R^{6B}$)$_n$N$R^{7A}R^{7B}$, wherein $R^{6A}$ and $R^{6B}$ can be independently selected from hydrogen, halogen, an optionally substituted $C_{1-4}$ alkyl, an optionally substituted $C_{1-4}$ haloalkyl and an optionally substituted $C_{3-8}$ cycloalkyl; $R^{7A}$ and $R^{7B}$ can be independently selected from hydrogen, an optionally substituted $C_{1-4}$ alkyl, an optionally substituted $C_{1-4}$ haloalkyl and an optionally substituted $C_{3-8}$ cycloalkyl; and n can be 0, 1, 2 or 3. In some embodiments, n can be 0. In other embodiments, n can be 1. In still other embodiments, n can be 2. In yet still other embodiments, n can be 3. In some embodiments, each $R^{6A}$ and each $R^{6B}$ can be independently hydrogen, halogen or an unsubstituted $C_{1-4}$ alkyl. In some embodiments, each $R^{6A}$ and each $R^{6B}$ can be independently hydrogen or an unsubstituted $C_{1-4}$ alkyl. In some embodiments, at least one of $R^{6A}$ and $R^{6B}$ can be hydrogen. In some embodiments, each $R^{6A}$ and each $R^{6B}$ can be hydrogen. In some embodiments, $R^{7A}$ and $R^{7B}$ can be independently hydrogen or an optionally substituted $C_{1-4}$ alkyl. In some embodiments, at least one of $R^{7A}$ and $R^{7B}$ can be hydrogen. In some embodiments, $R^{7A}$ and $R^{7B}$ can be each an optionally substituted $C_{1-4}$ alkyl. In some embodiments, $R^{7A}$ and $R^{7B}$ can be each an unsubstituted $C_{1-4}$ alkyl. When $R^3$ is substituted by —(C$R^{6A}R^{6B}$)$_n$N$R^{7A}R^{7B}$, —(C$R^{6A}R^{6B}$)$_n$N$R^{7A}R^{7B}$ can be —N(CH$_3$)$_2$, —(CH$_2$)N(CH$_3$)$_2$ or —(CH$_2$)$_2$N(CH$_3$)$_2$. In some embodiments, $R^3$ can be a lower alkylene-(mono-substituted alkyl amine). In other embodiments, $R^3$ can be a lower alkylene-(di-substituted alkyl amine).

Examples of $R^3$ moieties include, but are not limited to, the following:

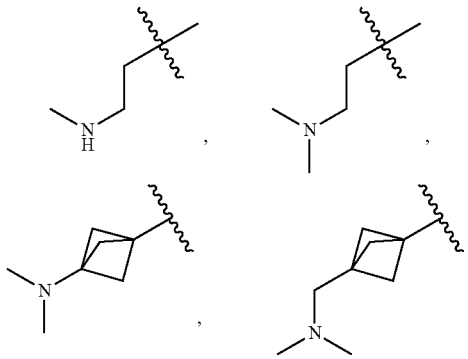

an optionally substituted

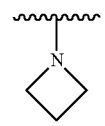 [SMILES: *N1CCC1]

(for example,

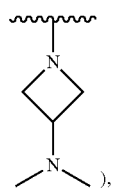

), an optionally substituted

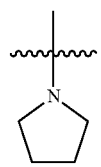 [SMILES: *N1CCCC1]

(for example,

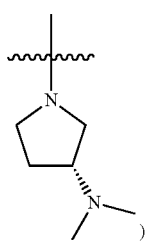 [SMILES: *N1CC[C@@H](N(C)C)C1]

)

and an optionally substituted

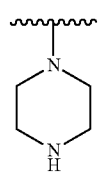

(for example

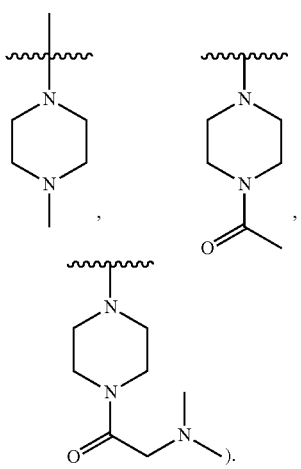

).

In some embodiments, $R^1$ can be hydrogen. In other embodiments, $R^1$ can be halogen. In still other embodiments, $R^1$ can be hydroxy. In yet still other embodiments, R can be cyano. In some embodiments, $R^1$ can be a substituted $C_{1-4}$ alkyl. In other embodiments, $R^1$ can be an unsubstituted $C_{1-4}$ alkyl. In still other embodiments, $R^1$ can be a substituted $C_{1-4}$ haloalkyl. In yet still other embodiments, $R^1$ can be an unsubstituted $C_{1-4}$ haloalkyl. In some embodiments, $R^1$ can be a substituted $C_{1-4}$ alkoxy. In other embodiments, $R^1$ can be an unsubstituted $C_{1-4}$ alkoxy. In still other embodiments, $R^1$ can be a substituted $C_{1-4}$ haloalkoxy. In yet other embodiments, $R^1$ can be an unsubstituted $C_{1-4}$ haloalkoxy. Example of suitable $R^1$ moieties include, but are not limited to, the following: chloro, fluoro, methyl, ethyl, n-propyl, iso-propyl, n-butyl, iso-butyl, tert-butyl, —$CF_3$, —$CHF_2$, —$CH_2F$, —$CH_2CF_3$, methoxy, ethoxy, n-propoxy, iso-propoxy, n-butoxy, iso-butoxy, tert-butoxy, —$OCF_3$, —$OCHF_2$, —$OCH_2F$ and —$OCH_2CF_3$.

In some embodiments, $A^1$ can be N (nitrogen) such that the ring shown in Formula (I) has the structure:

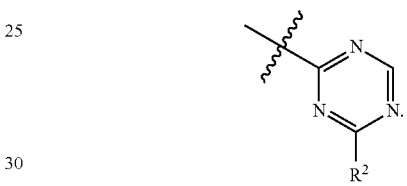

In some embodiments, $A^1$ can be $CR^8$ such that the ring shown in Formula (I) has the structure:

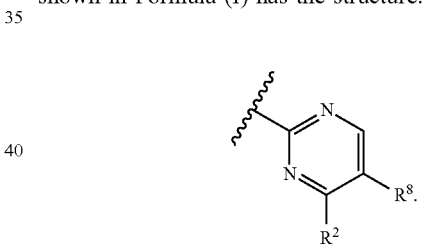

In some embodiments, $R^8$ can be hydrogen. In other embodiments, $R^8$ can be halogen. For example, $R^8$ can be chloro or fluoro. In still other embodiments, $R^8$ can be cyano. In yet still other embodiments, $R^8$ can be an optionally substituted $C_{1-4}$ alkyl. In some embodiments, $R^8$ can be an unsubstituted $C_{1-4}$ alkyl. In some embodiments, $R^8$ can be an unsubstituted $C_{1-4}$ haloalkyl or a substituted $C_{1-4}$ haloalkyl. An example of a suitable $C_{1-4}$ haloalkyl is $CF_3$. In some embodiments, $R^8$ can be an optionally substituted $C_{3-8}$ cycloalkyl. Examples of optionally substituted $C_{3-8}$ cycloalkyls are described herein and include, but are not limited to, an optionally substituted cyclopropyl, an optionally substituted cyclobutyl, an optionally substituted cyclopentyl, an optionally substituted bicyclo[1.1.1]pentyl, an optionally substituted cyclohexyl, an optionally substituted cycloheptyl and an optionally substituted cyclooctyl.

Examples of compounds of Formula (I) include the following:

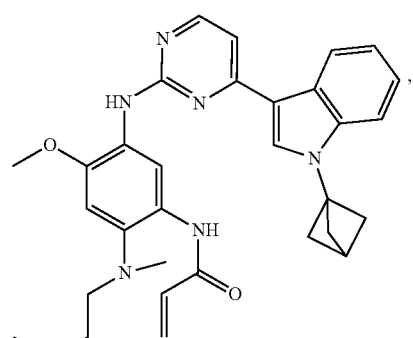
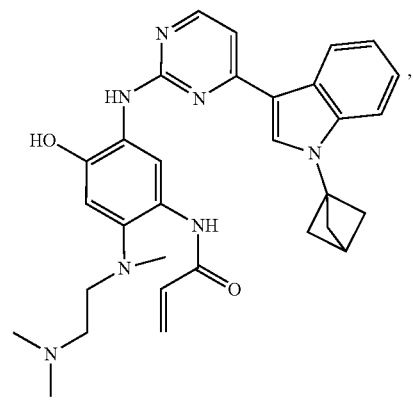
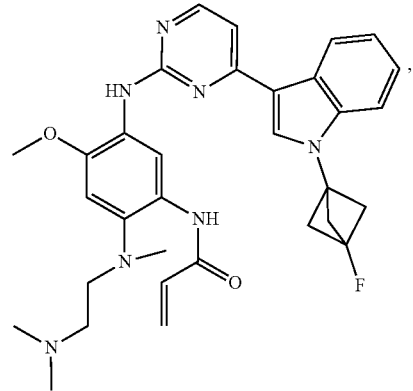
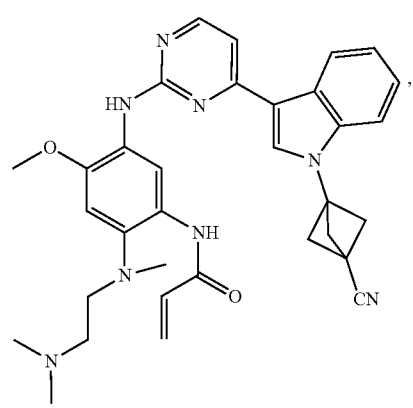
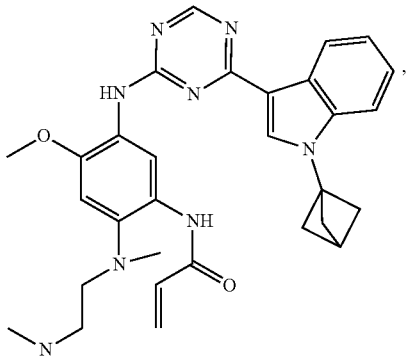
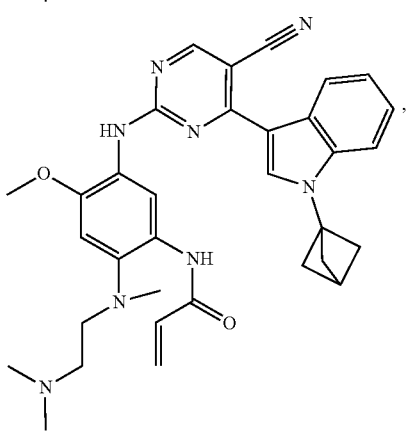
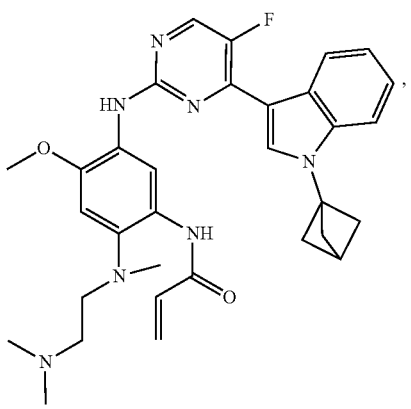
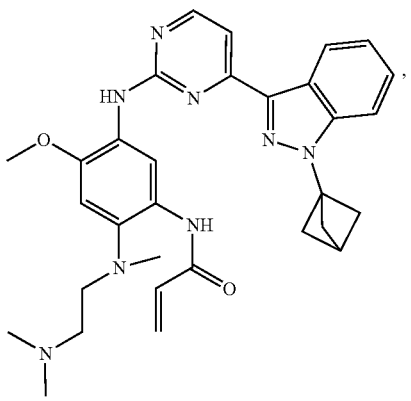

-continued
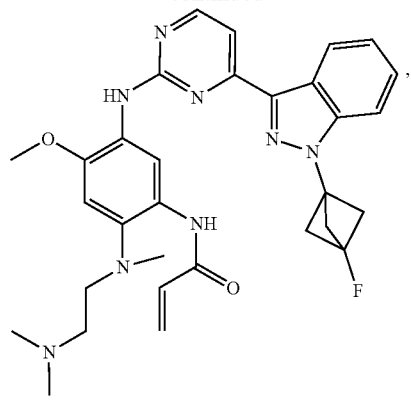
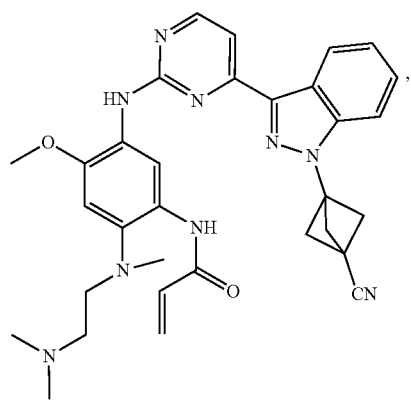
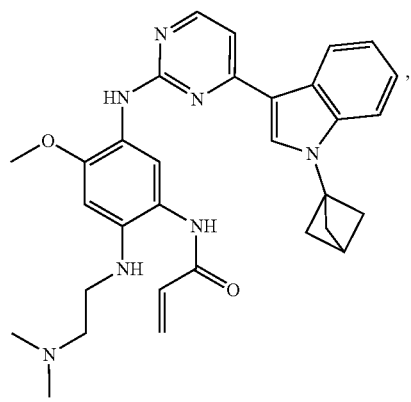
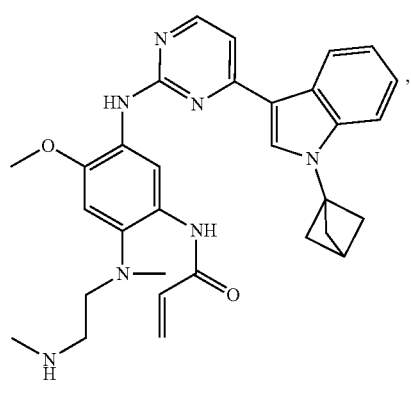
-continued
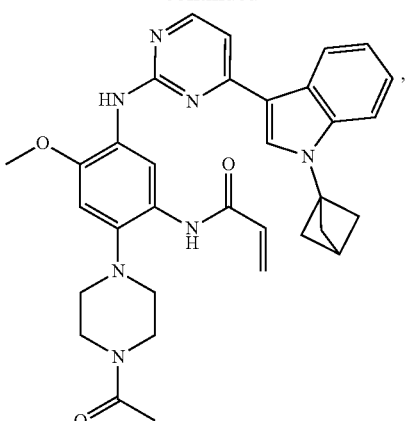
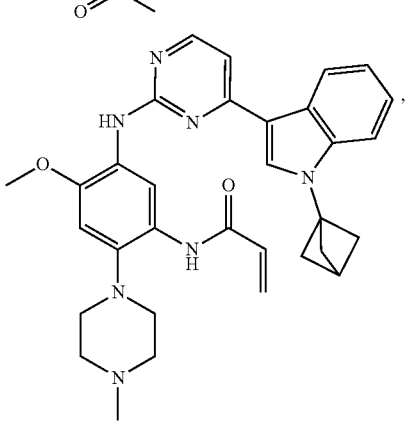
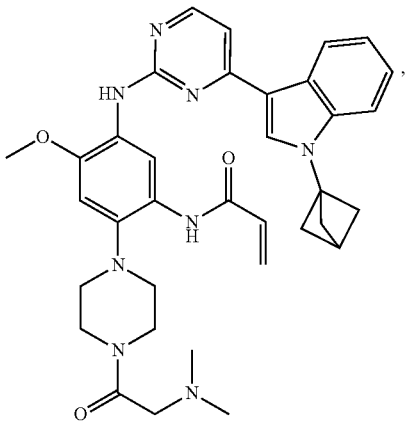
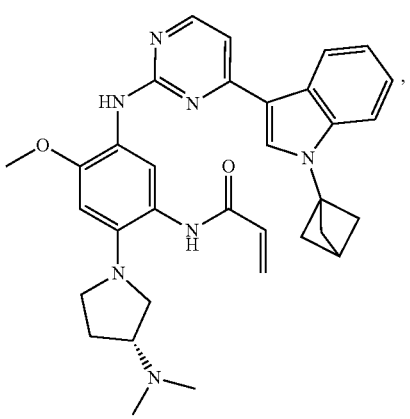

27

-continued

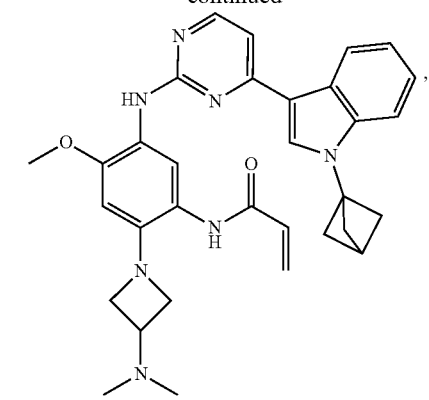

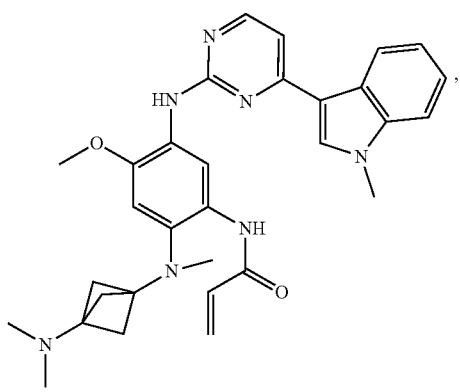

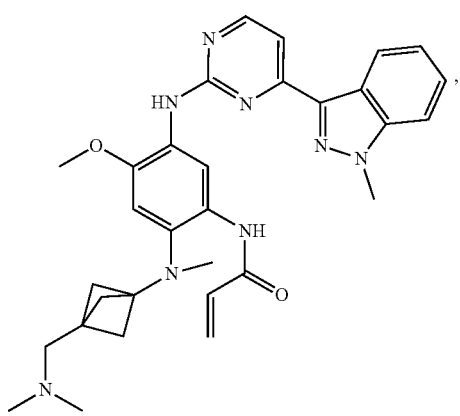

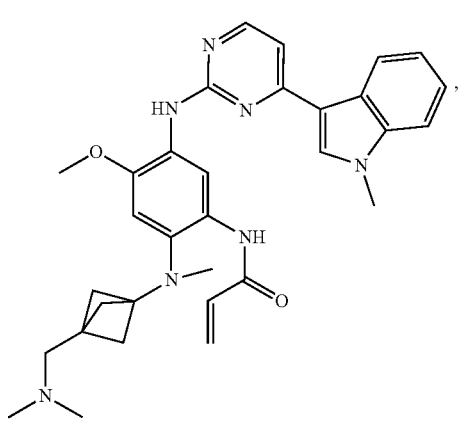

28

-continued

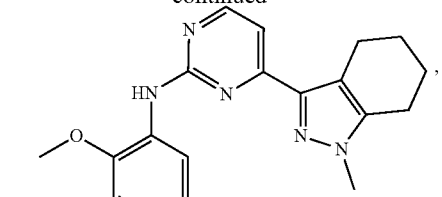

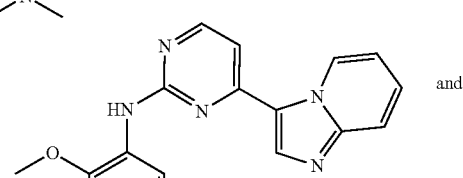

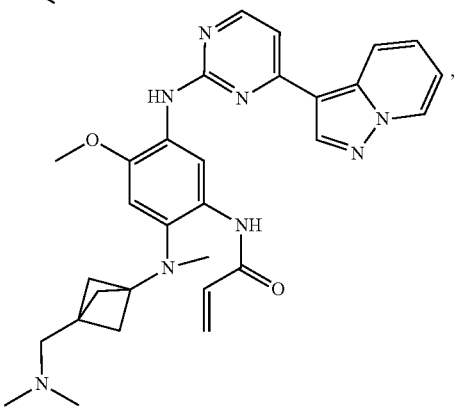 and or a pharmaceutically acceptable salt of any of the foregoing.

In some embodiments, $R^2$ can be substituted with bicyclo[1.1.1]pentyl. In some embodiments, $R^3$ can be a substituted bicyclo[1.1.1]pentyl.

Synthesis

Compounds of Formula (I), or a pharmaceutically acceptable salt thereof, and those described herein may be prepared in various ways. Some compounds of Formula (I), or a pharmaceutically acceptable salt thereof, can be obtained utilizing known synthetic procedures. General synthetic routes to the compounds of Formula (I), or a pharmaceutically acceptable salt thereof, and some examples of starting materials used to synthesize the compounds of Formula (I), or a pharmaceutically acceptable salt thereof, are shown and described herein. One example is shown below in Scheme 1. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

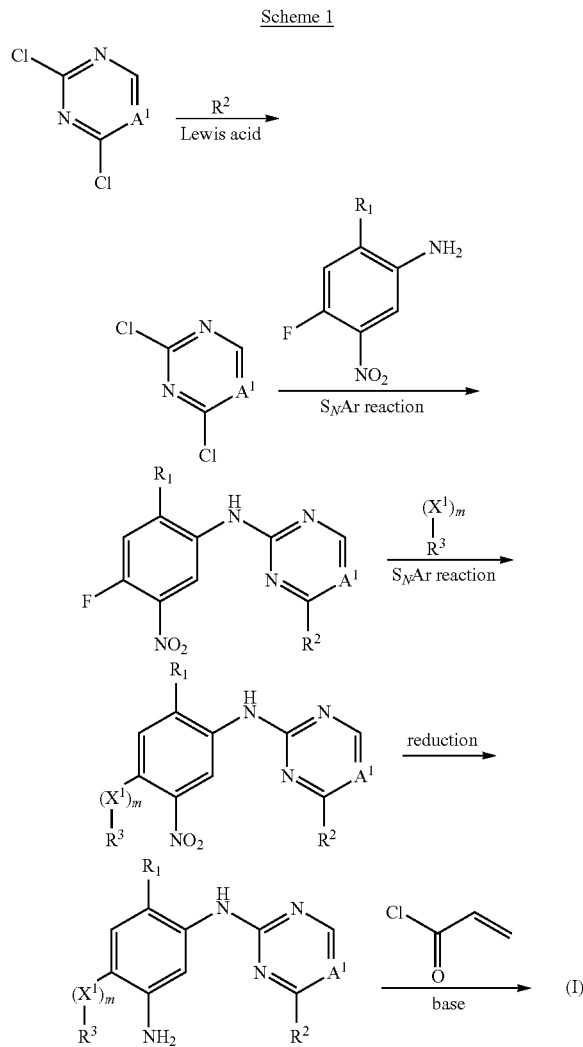

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

As described herein, compounds of Formula (I), or a pharmaceutically acceptable salt thereof, can be administered by a variety of methods. In some of the methods described herein, administration can be by injection, infusion and/or intravenous administration over the course of 1 minute, 5 minutes, 10 minutes, 30 minutes, 1 hour, 2 hours, 6 hours, 12 hours, 24 hours or longer, or any intermediate time. Other methods described herein can include oral, intravenous and/or intraperitoneal administration to a subject in need thereof, for example, to a subject to treat a cancer described herein responsive to an EGFR inhibitor.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer that can include contacting a malignant growth or a tumor, wherein the malignant growth or tumor is due to a cancer described herein.

Some embodiments described herein relate to a method for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated) that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a sample that includes a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated). Some embodiments described herein relate to a method for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated) that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a cancer cell from a cancer described herein. Other embodiments described herein relate to a method for inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated) that can include contacting a cancer cell from a cancer described herein with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), and thereby inhibiting the activity of EGFR.

Some embodiments described herein relate to a method for ameliorating or treating a cancer described herein that can include inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated) using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein by inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein by inhibiting the activity of EGFR (for example, inhibiting the activity of EGFR with acquired EGFR T790M mutation, inhibiting the activity of EGFR with a deletion in exon 19 (such as A740-A750), inhibiting the activity of EGFR with an insertion in exon 20, inhibiting the activity of EGFR with a mutation at L858R, inhibiting the activity of wildtype EGFR and/or where EGFR is overexpressed or activated). Some embodiments described herein relate to a method for ameliorating or treating a cancer described herein that can include contacting a cancer cell with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the compound inhibits the activity of EGFR (for example, a compound described herein can inhibits the activity of EGFR with acquired EGFR T790M mutation, inhibits the activity of EGFR with a deletion in exon 19 (such as A740-A750), inhibits the activity of EGFR with an insertion in exon 20, inhibits the activity of EGFR with a mutation at L858R, inhibits the activity of wildtype EGFR and/or where EGFR is overexpressed or activated).

Some embodiments disclosed herein relate to a method for inhibiting the activity of EGFR that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject or sample having a cancer cell selected from a lung cancer cell, a pancreatic cancer cell, a colon cancer cell, a breast cancer cell, a prostate cancer cell, a head and neck cancer cell, an ovarian cancer cell, a brain cancer cell and a kidney carcinoma cell, and wherein the EGFR has one or more selected from a deletion in exon 19, an insertion in exon 20, a mutation at L858R and an acquired EGFR T790M mutation. Other embodiments disclosed herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of EGFR, wherein the EGFR can have one or more selected from a deletion in exon 19, an insertion in exon 20, a mutation at L858R and an acquired EGFR T790M mutation. Still other embodiments disclosed herein relate to a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of EGFR, wherein the EGFR can have one or more selected from a deletion in exon 19, an insertion in exon 20, a mutation at L858R and an acquired EGFR T790M mutation.

Examples of suitable cancers include, but are not limited to: lung cancers (e.g., lung adenocarcinoma and non-small cell lung cancer), pancreatic cancers (e.g., pancreatic carcinoma such as, for example, exocrine pancreatic carcinoma), colon cancers (e.g., colorectal carcinomas, such as, for example, colon adenocarcinoma and colon adenoma), breast cancers, prostate cancers, head and neck cancers (e.g., squamous cell cancer of the head and neck), ovarian cancers, brain cancers (e.g., gliomas, such as glioma blastoma multiforme), and kidney carcinomas.

As described herein, a cancer can become resistant to one or more anti-cancer agents. In some embodiments, a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) can be used to treat and/or ameliorate a cancer that has become resistant to one or more anti-cancer agents (such as one or more EGFR inhibitors). Examples of anti-cancer agents that a subject may have developed resistance to include, but are not limited to, first generation EGFR inhibitors (such as gefitinib and erlotinib) and second generation EGFR inhibitors (for example, afatinib). In some embodiments, the cancer that has become resistant to one or more anti-cancer agents can be a cancer described herein.

Several known EGFR inhibitors can cause one or more undesirable side effects in the subject being treated. Two examples of these side effects are hyperglacemia and a rash. The rash can be characterized by mild scaling, pimples, roughness, a feeling of tightness, itching and/or burning. In some embodiments, a compound described herein (for example, a compound of Formula (I), or a pharmaceutically acceptable salt thereof) can decrease the number and/or severity of one or more side effects associated with a known EGFR inhibitor. In some embodiments, a compound of Formula (I), or a pharmaceutically acceptable salt thereof, can result in a severity of a side effect (such as one of those described herein) that is 25% less than compared to the severity of the same side effect experienced by a subject receiving a known EGFR inhibitor (such as gefitinib, erlotinib and/or afatinib). In some embodiments, a compound of Formula (I), or a pharmaceutically acceptable salt thereof, results in a number of side effects that is 25% less than compared to the number of side effects experienced by a subject receiving a known EGFR inhibitor (for example, gefitinib, erlotinib and/or afatinib). In some embodiments, a compound of Formula (I), or a pharmaceutically acceptable salt thereof, results in a severity of a side effect (such as one of those described herein) that is less in the range of about 10% to about 30% compared to the severity of the same side effect experienced by a subject receiving a known EGFR inhibitor (such as gefitinib, erlotinib and/or afatinib). In some embodiments, a compound of Formula (I), or a pharmaceutically acceptable salt thereof, results in a number of side effects that is in the range of about 10% to about 30% less than compared to the number of side effects experienced by a subject receiving a known EGFR inhibitor (for example, gefitinib, erlotinib and/or afatinib).

The one or more compounds of Formula (I), or a pharmaceutically acceptable salt thereof, that can be used to treat, ameliorate and/or inhibit the growth of a cancer wherein inhibiting the activity of EGFR is beneficial is provided in any of the embodiments described in paragraphs [0073]-[0094], under the heading titled "Compounds."

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance, and may positively affect one or more symptoms or aspects of the disease while having effects on other aspects of the disease or on unrelated systems that may be considered undesireable.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to treat, alleviate or ameliorate one or more symptoms or conditions of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein.

For example, an effective amount of a compound, or radiation, is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer) a therapeutically effective amount is that amount that alleviates or eliminates cough, shortness of breath and/or pain. As another example, an effective amount, or a therapeutically effective amount of an EGFR inhibitor is the amount which results in the reduction in EGFR activity and/or phosphorylation. The reduction in EGFR activity are known to those skilled in the art and can be determined by the analysis of EGFR intrinsic kinase activity and downstream substrate phosphorylation.

The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a cancer, are known to those skilled in the art. Example of suitable indicators include, but are not limited to, the reduction, alleviation or disappearance of one or more symptoms caused by the cancer, the reduction of tumor size, the elimination of the tumor, and/or long-term disease stabilization (growth arrest) of the tumor.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Intermediate 1

1-(bicyclo[1.1.1]pentan-1-yl)indolin-2-one

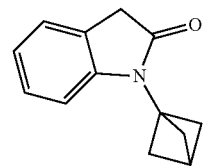 [SMILES: O=C1Cc2ccccc2N1C12CC(C1)C2]

Step 1: A solution of 2-(2-bromophenyl)acetic acid (22.0 g, 102.32 mmol) in DCM (400 mL) at 0° C. was treated with Hünig's base (53.47 mL, 306.97 mmol) followed by N1-((ethylimino)methylene)-N3,N3-dimethylpropane-1,3-diamine (29.42 g, 153.48 mmol), HOBt (21.41 g, 153.48 mmol), and bicyclo[1.1.1]pentan-1-amine hydrochloride (14.6 g, 122.78 mmol). The reaction was warmed to room temperature (RT) and stirred overnight. The reaction was concentrated in vacuo, adsorbed onto silica and purified by column chromatography ($SiO_2$, Hexanes/EtOAc) to provide the N-(bicyclo[1.1.1]pentan-1-yl)-2-(2-bromophenyl)acetamide (23.0 g, 80%) as a white solid. LC/MS (APCI) m/z 280.0 $[M+H]^+$.

Step 2: To a flame dried vial with stir bar was added compound N-(bicyclo[1.1.1]pentan-1-yl)-2-(2-bromophenyl)acetamide (5.0 g, 17.92 mmol), followed by $Pd(OAc)_2$ (1.2 g, 1.79 mmol), tri-tert-butylphosphonium tetrafluoroborate (1.03 g, 3.58 mmol), and $Cs_2CO_3$ (8.75 g, 26.88 mmol). The reaction vial was purged with Ar and degassed toluene (180 mL) was added. The mixture was heated at 100° C. for 4 h. The reaction was cooled to RT, and concentrated in vacuo to provide the crude product. Purification of the crude product by column chromatography (SiO$_2$, Hexanes/EtOAc) afforded 1-(bicyclo[1.1.1]pentan-1-yl)indolin-2-one (2.88 g, 81%) as a yellow solid. $^1$H NMR (400 MHz, CDCl$_3$) δ 7.26-7.19 (m, 2H), 7.09 (d, J=8.0 Hz, 1H), 7.01 (t, J=7.6, 1H), 3.46 (s, 2H), 2.59 (s, 1H), 2.46 (s, 6H); LC/MS (APCI) m/z 200.1 [M+H]$^+$.

Intermediate 2

1-(bicyclo[1.1.1]pentan-1-yl)indoline

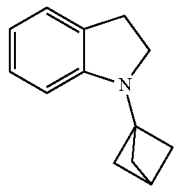 [SMILES: c1ccc2c(c1)CCN2C12CC(C1)C2]

Step 1: A flame-dried pressure tube was charged with 1,1-dibromo-2,2-bis(chloromethyl)cyclopropane (15 g, 50.5 mmol) and dibutyl ether (15 mL). The reaction was cooled to −45° C. and PhLi (53.2 mL, 101 mmol, 1.8M in dibutyl ether) was added slowly via syringe. The mixture was stirred at the same temperature for 5 mins. The reaction temperature was allowed to warm to 0° C. and stirred for 2 h in an ice bath at which point the reaction was brought to RT to provide a solution of crude [1.1.1]propellane.

Step 2: In a separate flask, a solution of indoline (11.4 mL, 101 mmol) in dibutyl ether (15 mL) was treated with iPrMgCl-LiCl (92 mL, 102 mmol, 1.11M in THF) via a dropping funnel at RT. After 2 h stirring at RT, the solution was added portion-wise to the aforementioned crude [1.1.1] propellane solution. The reaction vessel was capped with a Teflon™ pressure cap. The reaction was transferred to an oil bath and stirred at 60° C. for 16 h. The reaction was then removed from the oil bath, cooled in an ice bath and quenched slowly with sat. aq. NH$_4$Cl. The reaction was then diluted with EtOAc and transferred into a separation funnel. The layers were separated, and the combined organic layers were dried with Na$_2$SO$_4$, filtered, and concentrated under reduced pressure. The residual solvent was removed under vacuum, and the crude material was purified by column chromatography (SiO$_2$, Hexanes/EtOAc) to provide 1-(bicyclo[1.1.1]pentan-1-yl)indoline (2.20 g, 23%) as a yellow oil. $^1$H NMR (400 MHz, CDCl$_3$) δ 7.13-6.89 (m, 2H), 6.76 (d, J=7.8 Hz, 1H), 6.67 (dt, J=7.4, 0.9 Hz, 1H), 3.36 (t, J=8.4 Hz, 2H), 2.93 (t, J=8.4 Hz, 2H), 2.48 (s, 1H), 2.10 (s, 6H).

Intermediate 3

1-(bicyclo[1.1.1]pentan-1-yl)-1H-indole

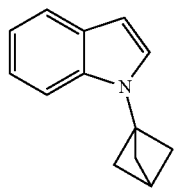 [SMILES: c1ccc2c(c1)ccn2C12CC(C1)C2]

Method A.

A solution of 1-(bicyclo[1.1.1]pentan-1-yl)indolin-2-one (3.6 g, 18.09 mmol) was cooled to 0° C. and treated with diisobutylaluminum hydride (1 M in toulene, 20.3 mL, 32.6 mmol) dropwise. The reaction was warmed to RT and stirred for 2 h. The mixture was cooled to 0° C. and quenched with MeOH (10 mL). The mixture was filtered through a celite pad with dichloromethane, dried over Na$_2$SO$_4$ and concentrated in vacuo. The residue was purified by column chromatography (SiO$_2$, Hexanes/EtOAc) to afford 1-(bicyclo[1.1.1]pentan-1-yl)-1H-indole (1.98 g, 60%) as a pale yellow oil. $^1$H NMR (400 MHz, CDCl$_3$) δ 7.62 (d, J=7.8 Hz, 1H), 7.56 (d, J=8.2 Hz, 1H), 7.22-7.18 (m, 1H), 7.13-7.08 (m, 1H), 7.07 (d, J=3.2 Hz, 1H), 6.46 (d, J=3.2 Hz, 1H), 2.67 (s, 1H), 2.42 (s, 6H); LC/MS (APCI) m/z 184.1 [M+H]$^+$.

Method B.

A solution of compound 1-(bicyclo[1.1.1]pentan-1-yl)indoline (100 mg, 0.54 mmol) in CH$_2$Cl$_2$ (5 mL) was treated with MnO$_2$ and stirred at RT. After 20 h, the reaction was filtered over Celite, and the Celite was washed with CH$_2$Cl$_2$. The combined filtrates were concentrated under vacuum to obtain 1-(bicyclo[1.1.1]pentan-1-yl)-1H-indole (79 mg, 80%) as a brown oil.

Example 1

N-(5-((4-(1-(bicyclo[1.1.1]pentan-1-yl)-1H-indol-3-yl)pyrimidin-2-yl)amino)-2-((2-(dimethylamino)ethyl)(methyl)amino)-4-methoxyphenyl)acrylamide

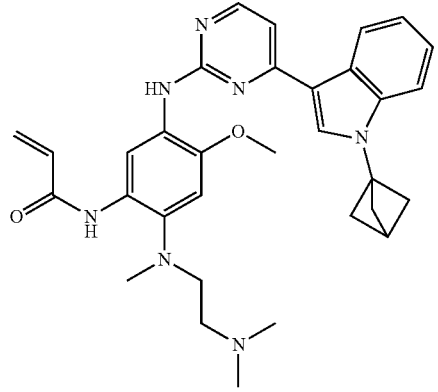 [SMILES: C=CC(=O)Nc1cc(Nc2nccc(-c3cn(C45CC(C4)C5)c4ccccc34)n2)c(OC)cc1N(C)CCN(C)C]

Step 1: To a stirred solution of 1-(bicyclo[1.1.1]pentan-1-yl)-1H-indole (580 mg, 3.27 mmol) in DME (10 mL) at RT was added 2,4-dichloropyrimidine (430 mg, 3.27 mmol) and aluminum chloride (654 mg, 4.90 mmol). The reaction was heated to 80° C. and stirred for 16 h. The mixture was then poured into ice cold water (100 mL), and the precipitate was collected by filtration to afford 1-(bicyclo[1.1.1]pentan-1-yl)-3-(2-chloropyrimidin-4-yl)-1H-indole (500 mg, 1.69 mmol, 53%) as off-white solid. LC/MS (ESI) m/z 296.1 [M+H]$^+$.

Step 2: To a stirred solution of 1-(bicyclo[1.1.1]pentan-1-yl)-3-(2-chloropyrimidin-4-yl)-1H-indole (525 mg, 1.77 mmol) in 2-pentanol (20 mL) at RT was added 4-fluoro-2-methoxy-5-nitroaniline (331 mg, 1.77 mmol) and p-toluenesulfonic acid (33 mg, 0.17 mmol). The reaction was heated to 80° C. and stirred for 16 h. The mixture was then poured into ice cold water (100 mL), and the precipitate was collected by filtration to afford 4-(1-(bicyclo[1.1.1]pentan-1-yl)-1H-indol-3-yl)-N-(4-fluoro-2-methoxy-5-nitrophenyl)

pyrimidin-2-amine (400 mg, 0.89 mmol, 80%) as off-white solid. LC/MS (ESI) m/z 446.1 [M+H]+.

Step 3: To a stirred solution of 4-(1-(bicyclo[1.1.1]pentan-1-yl)-1H-indol-3-yl)-N-(4-fluoro-2-methoxy-5-nitrophenyl)pyrimidin-2-amine (420 mg, 0.943 mmol) in DMA (15 mL) at RT was added N1,N1,N2-trimethylethane-1,2-diamine (0.2 mL, 1.42 mmol) and DIPEA (0.3 mL, 1.22 mmol). The mixture was warmed to 90° C. After 5 h, the reaction was cooled to RT, diluted with water (40 mL) and extracted with ethyl acetate (3×30 mL). The combined organic layers were washed with water (20 mL) and brine (20 mL), dried over sodium sulphate and concentrated to afford N1-(4-(1-(bicyclo[1.1.1]pentan-1-yl)-1H-indol-3-yl)pyrimidin-2-yl)-N4-(2-(dimethylamino)ethyl)-2-methoxy-N4-methyl-5-nitrobenzene-1,4-diamine (350 mg, 0.66 mmol, 70%) as a bright red colored solid. LC/MS (ESI) m/z 528.1 [M+H]+.

Step 4: To a stirred solution of N1-(4-(1-(bicyclo[1.1.1]pentan-1-yl)-1H-indol-3-yl)pyrimidin-2-yl)-N4-(2-(dimethylamino)ethyl)-2-methoxy-N4-methyl-5-nitrobenzene-1,4-diamine (380 mg, 0.72 mmol) in THF:EtOAc (1:1, 10 mL) was added 10% Pd/C (150 mg), and the reaction was stirred at RT under hydrogen (1 atm) for 2 h. The mixture was filtered through celite and was concentrated in vacuo to afford N4-(4-(1-(bicyclo[1.1.1]pentan-1-yl)-1H-indol-3-yl)pyrimidin-2-yl)-N1-(2-(dimethylamino)ethyl)-5-methoxy-N1-methylbenzene-1,2,4-triamine (350 mg, 0.70 mmol, 96%) as an off-white solid. LC/MS (ESI) m/z 498.4 [M+H]+.

Step 5: To a stirred solution of N4-(4-(1-(bicyclo[1.1.1]pentan-1-yl)-1H-indol-3-yl)pyrimidin-2-yl)-N1-(2-(dimethylamino)ethyl)-5-methoxy-N1-methylbenzene-1,2,4-triamine (200 mg, 0.40 mmol) in THF and water (1:1, 10 mL) at 0° C. was added DIPEA (0.2 mL, 0.80 mmol) followed by acryloyl chloride (0.05 mL, 0.60 mmol). After 30 mins, the mixture was diluted with water (30 mL) and extracted with ethyl acetate (3×20 mL). The combined organic layers were washed with water (20 mL) and brine (20 mL), dried over sodium sulphate and concentrated in vacuo. The resultant residue was purified by Reveleris C-18 reverse phase column using 30% aqueous formic acid (0.1%) in acetonitrile to afford N-(5-(4-(1-(bicyclo[1.1.1]pentan-1-yl)-1H-indol-3-yl)pyrimidin-2-ylamino)-2-((2-(dimethyl amino)ethyl)(methyl)amino)-4-methoxyphenyl)acrylamide (70 mg, 0.12 mmol, 35%) as an off-white solid. 1H NMR (300 MHz, DMSO-d6) δ 10.1 (s, 1H), 8.84 (s, 1H), 8.32-8.16 (m, 3H), 7.99 (s, 1H), 7.66 (d, J=8.4 Hz, 1H), 7.26 (d, J=5.4 Hz, 1H), 7.19 (dd, J=7.2, 7.2 Hz, 1H), 7.09 (dd, J=7.2, 7.8 Hz, 1H), 7.01 (s, 1H), 6.44-6.35 (m, 1H), 6.19 (dd, J=1.8, 16.8 Hz, 1H), 5.70 (dd, J=1.8, 10.2 Hz, 1H), 3.80 (s, 3H), 2.88 (t, J=5.4 Hz, 2H), 2.70 (s, 3H), 2.69 (s, 1H), 2.43 (s, 6H), 2.32 (t, J=5.4 Hz, 2H), 2.21 (s, 6H); LC/MS (ESI) m/z 552.5 [M+H]+.

Intermediate 4

3-(1H-indol-1-yl)bicyclo[1.1.1]pentane-1-carbonitrile

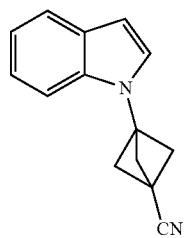 [SMILES: N#CC12CC(n3ccc4ccccc43)(C1)C2]

Step 1: To a solution of 2-(2-bromophenyl)acetic acid (1.17 g, 5.44 mmol) in DCM (18.14 mL) was added N,N-Diisopropylethylamine (2.369 mL, 13.60 mmol), followed by N-(3-Dimethylaminopropyl)-N'-ethylcarbodiimide (1.267 g, 8.16 mmol) and HOBt(monohydrate) (1.250 g, 8.16 mmol). To this mixture was added methyl 3-aminobicyclo[1.1.1]pentane-1-carboxylate hydrochloride (0.966 g, 5.44 mmol). The mixture was stirred overnight at RT. LCMS showed the formation of product. The reaction was diluted with ethyl acetate and water. The organic layer was separated and washed with sat. aq. ammonium chloride. The organic layer was dried over Na2SO4, concentrated and purified by column chromatography (SiO2, hexanes/EtOAc) to afford methyl 3-(2-(2-bromophenyl)acetamido)bicyclo[1.1.1]pentane-1-carboxylate (1.51 g, 4.46 mmol, 82%). LC/MS (ESI) m/z 338.0 [M+H]+.

Step 2: To a mixture of methyl 3-(2-(2-bromophenyl)acetamido)bicyclo[1.1.1]pentane-1-carboxylate (1.58 g, 4.67 mmol), tri-t-butylphosphonium tetrafluoroborate, 99% (0.271 g, 0.934 mmol), palladium(II) acetate (0.105 g, 0.467 mmol) and cesium carbonate (1.352 g, 7.01 mmol), was added toluene (23.36 mL). The mixture was flushed with N2 for several minutes and then heated at 100° C. for 4 h. The mixture was then filtered through pad of celite. The filtrate was concentrated in vacuo, adsorbed on celite and purified by column chromatography (SiO2, hexanes/EtOAc) to afford methyl 3-(2-oxoindolin-1-yl)bicyclo[1.1.1]pentane-1-carboxylate (639 mg, 2.484 mmol, 53.2%). LC/MS (ESI) m/z 258.1 [M+H]+.

Step 3: To a solution of methyl 3-(2-oxoindolin-1-yl)bicyclo[1.1.1]pentane-1-carboxylate (1.28 g, 4.98 mmol) in THF (24.88 mL) was added Diisobutylaluminum hydride solution (1M in THF, 29.9 mL, 29.9 mmol) at 0° C. The reaction was slowly warmed to RT and stirred for 1 h. The reaction was quenched with MeOH (6 mL) and then diluted with ethyl acetate and sat. aq. ammonium chloride. An emulsion was formed which was passed through a celite pad. The filtrate was collected, concentrated and purified by column chromatography (SiO2, hexanes/EtOAc) to afford (3-(1H-indol-1-yl)bicyclo[1.1.1]pentan-1-yl)methanol (720 mg, 3.38 mmol, 67%). LC/MS (ESI) m/z 214.1 [M+H]+.

Step 4: To a solution of (3-(1H-indol-1-yl)bicyclo[1.1.1]pentan-1-yl)methanol (100 mg, 0.469 mmol) in acetonitrile (1407 μl) and water (156 μl) was added 2,2,6,6-Tetramethylpiperdine 1-oxly (7.33 mg, 0.047 mmol) and ammonium acetate (181 mg, 2.344 mmol). Iodosobenzene I,I-diacetate (332 mg, 1.032 mmol) was then added. The mixture was stirred at RT for 2 h and then concentrated in vacuo. The crude product was diluted with ethyl acetate and water. The organic layer was separated, washed with sat. aq. sodium thiosulfate, dried over Na2SO4, concentrated and purified by column chromatography (SiO2, hexanes/EtOAc) to afford 3-(1H-indol-1-yl)bicyclo[1.1.1]pentane-1-carbonitrile (21 mg, 0.101 mmol, 21%). 1H NMR (400 MHz, CDCl3) δ 7.65-7.60 (m, 1H), 7.42-7.40 (m, 1H), 7.26-7.25 (m, 1H), 7.16-7.14 (m, 1H), 6.97 (s, 1H), 6.50 (s, 1H), 2.87 (s, 6H); LC/MS (ESI) m/z 209.1 [M+H]+.

Example 2

N-(5-((4-(1-(3-cyanobicyclo[1.1.1]pentan-1-yl)-1H-indol-3-yl)pyrimidin-2-yl)amino)-2-((2-(dimethylamino)ethyl)(methyl)amino)-4-methoxyphenyl)acrylamide

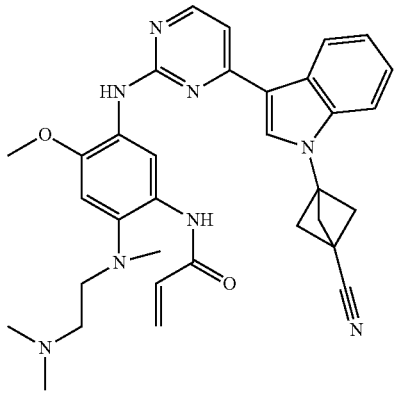 [SMILES: C=CC(=O)Nc1cc(Nc2nccc(-c3cn(C45CC(C#N)(C4)C5)c4ccccc34)n2)c(OC)cc1N(C)CCN(C)C]

Step 1: To a solution of 2,4-dichloropyrimidine (172 mg, 1.152 mmol) in DME (3201 μL) was added 3-(1H-indol-1-yl)bicyclo[1.1.1]pentane-1-carbonitrile (200 mg, 0.960 mmol) and aluminum trichloride (192 mg, 1.441 mmol). The mixture was heated to 80° C. and stirred for 10 h. The mixture was diluted with ethyl acetate and water, and then passed through a pad of celite. The organic layer from the collected filtrate was separated, dried over Na$_2$SO$_4$, concentrated and purified by column chromatography (SiO$_2$, hexanes/EtOAc) to afford 3-(3-(2-chloropyrimidin-4-yl)-1H-indol-1-yl)bicyclo[1.1.1]pentane-1-carbonitrile (168 mg, 0.524 mmol, 54%). LC/MS (ESI) m/z 321.1 [M+H]$^+$.

Step 2: To a solution of 3-(3-(2-chloropyrimidin-4-yl)-1H-indol-1-yl)bicyclo[1.1.1]pentane-1-carbonitrile (168 mg, 0.524 mmol) in 2-propanol (5.23 mL) was added 4-fluoro-2-methoxy-5-nitroaniline (97 mg, 0.524 mmol) followed by 4-methylbenzenesulfonic acid hydrate (19.92 mg, 0.105 mmol). The mixture was heated at 80° C. for 10 h. Additional 4-fluoro-2-methoxy-5-nitroaniline (19.4 mg, 0.104 mmol) and 2-propanol (2 mL) was added to the reaction, and the mixture was heated for 3 h at 80° C. The reaction was cooled to RT and concentrated in vacuo. The resulting residue was diluted with ethyl acetate and water. The organic layer was separated, washed with sat. aq. sodium bicarbonate and brine, dried over Na$_2$SO$_4$ and concentrated. The resulting residue was triturated with diethyl ether to afford 3-(3-(2-((4-fluoro-2-methoxy-5-nitrophenyl)amino)pyrimidin-4-yl)-1H-indol-1-yl)bicyclo[1.1.1]pentane-1-carbonitrile (182 mg, 0.387 mmol, 73%). LC/MS (ESI) m/z 471.1 [M+H]$^+$.

Step 3: To a solution of 3-(3-(2-((4-fluoro-2-methoxy-5-nitrophenyl)amino)pyrimidin-4-yl)-1H-indol-1-yl)bicyclo[1.1.1]pentane-1-carbonitrile (180 mg, 0.383 mmol) in DMA (3826 μL) was added N,N-Diisopropylethylamine (133 μL, 0.765 mmol) followed by N1,N1,N2-trimethylethane-1,2-diamine (58.6 mg, 0.574 mmol). The mixture was heated at 70° C. for 2 h. The mixture was then poured into cold water and extracted with ethyl acetate (3×50 mL). The combined organic layers were washed with water and brine, dried over Na$_2$SO$_4$, and concentrated. The crude product was purified by column chromatography (SiO$_2$, CH$_2$Cl$_2$/MeOH) to afford 3-(3-(2-((4-((2-(dimethylamino)ethyl)(methyl)amino)-2-methoxy-5-nitrophenyl)amino)pyrimidin-4-yl)-1H-indol-1-yl)bicyclo[1.1.1]pentane-1-carbonitrile (120 mg, 0.217 mmol, 56%). LC/MS (ESI) m/z 553.3 [M+H]$^+$.

Step 4: To a solution of 3-(3-(2-((4-((2-(dimethylamino)ethyl)(methyl)amino)-2-methoxy-5-nitrophenyl)amino)pyrimidin-4-yl)-1H-indol-1-yl)bicyclo[1.1.1]pentane-1-carbonitrile (50 mg, 0.090 mmol) in 6 N aq. HCl (1.81 mL) was added Iron (50.5 mg, 0.905 mmol). The mixture was heated at 60° C. for 45 mins. The reaction was then cooled to RT and filtered. The solvents were evaporated, and the residue was triturated with ether. The precipitate formed was filtered and dried to afford 3-(3-(2-((5-amino-4-((2-(dimethylamino)ethyl)(methyl)amino)-2-methoxyphenyl)amino)pyrimidin-4-yl)-1H-indol-1-yl)bicyclo[1.1.1]pentane-1-carbonitrile hydrochloride (50 mg, 0.089 mmol, 99%), which was used in the next step without further purification. LC/MS (ESI) m/z 523.3 [M+H]$^+$.

Step 5: To a solution of 3-(3-(2-((5-amino-4-((2-(dimethylamino)ethyl)(methyl)amino)-2-methoxyphenyl)amino)pyrimidin-4-yl)-1H-indol-1-yl)bicyclo[1.1.1]pentane-1-carbonitrile hydrochloride (50 mg, 0.089 mmol) in THF (1.72 mL) and DMF (0.52 mL) was added DIPEA (156 μl, 0.894 mmol) at 0° C. To this mixture was added acryloyl chloride (8.09 mg, 0.089 mmol) in THF (0.2 mL). The mixture was stirred at 0° C. for 10 mins and then diluted with ethyl acetate and water. The organic layer was separated, dried over Na$_2$SO$_4$, and concentrated. The crude product was purified by HPLC (10:90 to 80:20 0.1% HCO$_2$H (aq): MeCN) to afford N-(5-((4-(1-(3-cyanobicyclo[1.1.1]pentan-1-yl)-1H-indol-3-yl)pyrimidin-2-yl)amino)-2-((2-(dimethylamino)ethyl)(methyl)amino)-4-methoxyphenyl)acrylamide (6 mg, 10.40 μmol, 11%). $^1$H NMR (400 MHz, DMSO-d$_6$) δ 10.05 (s, 1H), 8.81 (s, 1H), 8.40-8.30 (m, 3H), 8.19 (s, 1H), 7.72-7.70 (m, 1H), 7.33-7.31 (m, 2H), 7.29-7.27 (m, 1H), 7.06 (s, 1H), 6.55-6.47 (m, 1H), 5.81-5.78 (m, 1H), 3.87 (s, 3H), 3.02-3.01 (m, 8H), 2.75 (s, 3H), 2.60-2.28 (m, 9H); LC/MS (ESI) m/z 577.3 [M+H]$^+$.

Example 3

N-(5-((4-(1-(bicyclo[1.1.1]pentan-1-yl)-1H-indol-3-yl)-5-cyanopyrimidin-2-yl)amino)-2-((2-(dimethylamino)ethyl)(methyl)amino)-4-methoxyphenyl)acrylamide

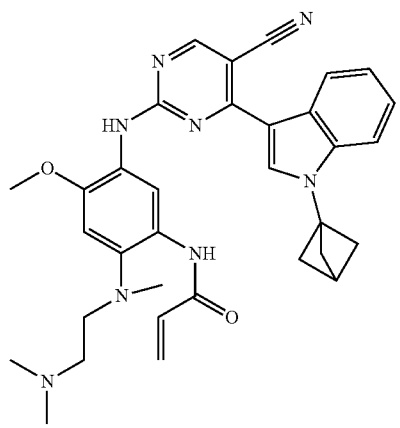 [SMILES: C=CC(=O)Nc1cc(Nc2ncc(C#N)c(-c3cn(C45CC(C4)C5)c4ccccc34)n2)c(OC)cc1N(C)CCN(C)C]

Step 1: To a solution of 2,4-dichloropyrimidine-5-carbonitrile (500 mg, 2.87 mmol) in dimethoxy ethane (14.4 mL) was added 1-(bicyclo[1.1.1]pentan-1-yl)-1H-indole (527 mg, 2.87 mmol, from example 1, step-3) and aluminum trichloride (575 mg, 4.31 mmol). The mixture was heated at 80° C. for 2 h, cooled to RT, and diluted with ethyl acetate/water. The organic layer was separated, dried over Na$_2$SO$_4$, concentrated and purified by column chromatography using 0-20% ethyl acetate in hexane to afford impure product (eluting along with dialkylated product). The impure compound was again purified by silica gel chromatography (SiO$_2$, hexanes/EtOAc) to afford 4-(1-(bicyclo[1.1.1]pentan-1-yl)-1H-indol-3-yl)-2-chloropyrimidine-5-carbonitrile (195 mg, 0.608 mmol, 21%). LC/MS (ESI) m/z 321.1 [M+H]$^+$.

Step 2: To a solution of 4-(1-(bicyclo[1.1.1]pentan-1-yl)-1H-indol-3-yl)-2-chloropyrimidine-5-carbonitrile (20 mg, 0.062 mmol) in 2-propanol (0.623 mL) was added 4-fluoro-2-methoxy-5-nitroaniline (11.61 mg, 0.062 mmol) followed by 4-methylbenzenesulfonic acid hydrate (2.372 mg, 0.012 mmol). The mixture was heated at 80° C. for 6 h. The reaction was cooled to RT. The resulting precipitate was filtered, washed with cold 2-propanol and dried to afford 4-(1-(bicyclo[1.1.1]pentan-1-yl)-1H-indol-3-yl)-2-((4-fluoro-2-methoxy-5-nitrophenyl)amino)pyrimidine-5-carbonitrile (21 mg, 0.045 mmol, 71%), which was used in the next step without purification. LC/MS (ESI) m/z 471.2 [M+H]$^+$.

Step 3: To a solution of 4-(1-(bicyclo[1.1.1]pentan-1-yl)-1H-indol-3-yl)-2-((4-fluoro-2-methoxy-5-nitrophenyl)amino)pyrimidine-5-carbonitrile (100 mg, 0.213 mmol) in DMA (3 mL) was added N,N-Diisopropylethylamine (0.074 mL, 0.425 mmol) followed by N1,N1,N2-trimethylethane-1,2-diamine (21.72 mg, 0.213 mmol) in DMA (0.2 mL). The mixture was heated at 70° C. for 1 h. The mixture was then cooled to RT, poured into cold water and extracted with ethyl acetate. The combined organic layers were washed with brine, dried over Na$_2$SO$_4$, concentrated and purified by column chromatography (SiO$_2$, CH$_2$Cl$_2$/MeOH) to afford 4-(1-(bicyclo[1.1.1]pentan-1-yl)-1H-indol-3-yl)-2-((4-((2-(dimethylamino)ethyl)(methyl)amino)-2-methoxy-5-nitrophenyl)amino)pyrimidine-5-carbonitrile (78 mg, 0.141 mmol, 66%). LC/MS (ESI) m/z 553.1 [M+H]$^+$.

Step 4: To a solution of 4-(1-(bicyclo[1.1.1]pentan-1-yl)-1H-indol-3-yl)-2-((4-((2-(dimethylamino)ethyl)(methyl)amino)-2-methoxy-5-nitrophenyl)amino)pyrimidine-5-carbonitrile (50 mg, 0.090 mmol) in aq. HCl (2 mL, 12.0 mmol) was added Iron (50 mg, 0.895 mmol). The mixture was heated to 70° C. After 30 mins the reaction was cooled to RT. The reaction was concentrated in vacuo, and the resulting residue was triturated with ether. The precipitate was collected and dried to afford 2-((5-amino-4-((2-(dimethylamino)ethyl)(methyl)amino)-2-methoxyphenyl)amino)-4-(1-(bicyclo[1.1.1]pentan-1-yl)-1H-indol-3-yl)pyrimidine-5-carbonitrile hydrochloride (50 mg, 0.089 mmol, 99%), which was used in the next step without further purification. LC/MS (ESI) m/z 523.1 [M+H]$^+$.

Step 5: To a solution of 2-((5-amino-4-((2-(dimethylamino)ethyl)(methyl)amino)-2-methoxyphenyl)amino)-4-(1-(bicyclo[1.1.1]pentan-1-yl)-1H-indol-3-yl)pyrimidine-5-carbonitrile (47 mg, 0.090 mmol) in tetrahydrofuran (4 mL) was added N,N-Diisopropylethylamine (0.078 mL, 0.450 mmol) at 0° C. followed by acryloyl chloride (8.14 mg, 0.090 mmol) in THF (0.2 mL). The mixture was stirred at 0° C. for 10 mins at which point additional acryloyl chloride (1.62 mg, 0.018 mmol) was added at 0° C. After 10 mins, the reaction was diluted with ethyl acetate and water. The organic layer was washed with water and brine, dried over Na$_2$SO$_4$, concentrated and was purified by HPLC (10:90 to 80:20 0.1% HCO$_2$H (aq): MeCN) to afford N-(5-((4-(1-(bicyclo[1.1.1]pentan-1-yl)-1H-indol-3-yl)-5-cyanopyrimidin-2-yl)amino)-2-((2-(dimethylamino)ethyl)(methyl)amino)-4-methoxyphenyl)acrylamide (15 mg, 0.026 mmol, 28.9%). $^1$H NMR (400 MHz, CDCl$_3$) δ 10.08 (s, 1H), 9.47 (s, 1H), 8.70 (s, 1H), 8.38-8.35 (m, 2H), 7.71-7.69 (m, 1H), 7.23-7.20 (m, 1H), 7.07-7.05 (m, 1H), 6.43-6.39 (m, 1H), 6.20-6.16 (m, 1H), 5.74-5.71 (m, 1H), 3.73 (s, 3H), 2.93-2.92 (m, 2H), 2.76 (s, 3H), 2.75 (s, 1H), 2.49 (s, 6H), 2.48-2.38 (m, 2H), 2.21 (s, 6H); LC/MS (ESI) m/z 577.3 [M+H]$^+$.

Intermediate 5

3-((dimethylamino)methyl)-N-methylbicyclo[1.1.1]pentan-1-amine

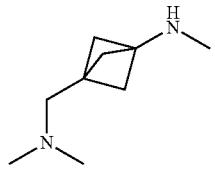

Step 1: To a solution of 3-(methoxycarbonyl)bicyclo[1.1.1]pentane-1-carboxylic acid (5 g, 29.4 mmol) at 0° C. was added oxalyl chloride (7.57 mL, 88 mmol) and dimethylformamide (0.023 mL, 0.294 mmol). The mixture was stirred at RT for 2 h. The solvents were evaporated. The crude was re-dissolved in dichloromethane (50 mL) and a solution of dimethylamine (2M in MeOH, 29.4 mL, 58.8 mmol) in dichloromethane (50 mL) was added at 0° C. The mixture was stirred at 0° C. for 1 h and then partitioned between DCM/water. The organic layer was separated, dried over Na$_2$SO$_4$, and concentrated in vacuo to afford methyl 3-(dimethylcarbamoyl)bicyclo[1.1.1]pentane-1-carboxylate (5.67 g, 28.7 mmol, 98%) as an off-white solid. LC/MS (APCI) m/z 198.1 [M+H]$^+$.

Step 2: To a solution of methyl 3-(dimethylcarbamoyl)bicyclo[1.1.1]pentane-1-carboxylate (5.67 g, 28.7 mmol) in tetrahydrofuran (40.0 mL) and H$_2$O (13.3 mL) was added lithium hydroxide monohydrate (1.810 g, 43.1 mmol) at 0° C. The mixture warmed RT and stirred over 2 days. The organic solvent was removed in vacuo, and the reaction was diluted with water. To this mixture was added Dowex® Marathon™ C hydrogen form (60 g), and the reaction was stirred for 1 h. The reaction was filtered, and the filtrate was concentrated to afford 3-(dimethylcarbamoyl)bicyclo[1.1.1]pentane-1-carboxylic acid (5.1 g, 27.8 mmol, 97%) as a white solid. LC/MS (APCI) m/z 184.1 [M+H]$^+$.

Step 3: To a solution of 3-(dimethylcarbamoyl)bicyclo[1.1.1]pentane-1-carboxylic acid (331 mg, 1.81 mmol) in tBuOH (9.0 mL) was added 3 Å molecular sieves (400 mg) followed by triethylamine (0.504 mL, 3.61 mmol) and diphenyl phosphorazidate (0.466 mL, 2.17 mmol). The mixture was stirred at 30° C. for 2 h and then heated to 85° C. overnight. The reaction was concentrated in vacuo and purified by column chromatography (SiO$_2$, DCM/MeOH) to afford tert-butyl (3-(dimethylcarbamoyl)bicyclo[1.1.1]pentan-1-yl)carbamate (160 mg, 1.81 mmol, 35%) as a colorless oil. LC/MS (APCI) m/z 155.1 [C$_{13}$H$_{22}$N$_2$O$_3$—C$_5$H$_9$O$_2$+H]$^+$.

Step 4: A solution of tert-butyl (3-(dimethylcarbamoyl)bicyclo[1.1.1]pentan-1-yl)carbamate (350 mg, 1.38 mmol) in THF (6.9 mL) was cooled to 0° C. and treated with NaH (60% dispersion in mineral oil, 83 mg, 2.06 mmol). After 10 mins, iodomethane (258 μL, 4.1 mmol) was added. After 16 h, additional iodomethane (258 μL, 4.1 mmol) was added. After 2 h, the reaction was quenched by the addition of water. The mixture was diluted with EtOAc and H₂O, and extracted with EtOAc. The combined organic layers were dried over Na₂SO₄ and concentrated in vacuo to afford the crude product which was purified by column chromatography (SiO₂, DCM/MeOH) to afford tert-butyl (3-(dimethylcarbamoyl)bicyclo[1.1.1]pentan-1-yl)(methyl)carbamate (209.4 mg, 57%) as a colorless oil. LC/MS (APCI) m/z 169.1 $[C_{14}H_{24}N_2O_3—C_5H_9O_2+H]^+$.

Step 5: A solution of tert-butyl (3-(dimethylcarbamoyl)bicyclo[1.1.1]pentan-1-yl)(methyl)carbamate (209.0 mg, 1.38 mmol) in THF (3.1 mL) was cooled to 0° C. and then was treated with BH₃-THF (1M in THF, 3.12 mL, 3.12 mmol). The reaction was warmed to 35° C. and stirred for 3 h, and then for 4 days at 45° C. The reaction was quenched at 0° C. by the addition of MeOH. The mixture was concentrated in vacuo, diluted with MeOH and reconcentrated (3×). The crude product was purified by reverse phase HPLC using 20-60% acetonitrile in water to afford tert-butyl (3-((dimethylamino)methyl)bicyclo[1.1.1]pentan-1-yl)(methyl)carbamate (196 mg, 99%) as a colorless oil. LC/MS (APCI) m/z 255.2 $[M+H]^+$.

Step 6: A solution of tert-butyl (3-((dimethylamino)methyl)bicyclo[1.1.1]pentan-1-yl)(methyl)carbamate (198 mg, 0.778 mmol) in EtOAc (3.89 mL) was cooled to 0° C. and treated with hydrogen chloride (4M in Dioxane, 1.95 mL, 7.78 mmol). The mixture was stirred for 2 h at RT. The reaction was then concentrated to provide 3-((dimethylamino)methyl)-N-methylbicyclo[1.1.1]pentan-1-amine dihydrochloride (170 mg, 96%) as an off-white solid. LC/MS (APCI) m/z 155.2 $[M+H]^+$.

Example 4

N-(2-((3-((dimethylamino)methyl)bicyclo[1.1.1]pentan-1-yl)(methyl)amino)-4-methoxy-5-((4-(1-methyl-1H-indol-3-yl)pyrimidin-2-yl)amino)phenyl)acrylamide

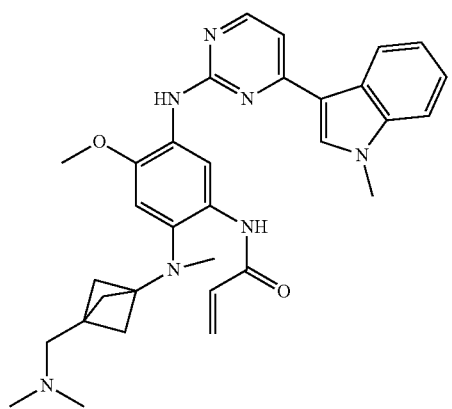 [SMILES: C=CC(=O)Nc1cc(Nc2nccc(-c3cn(C)c4ccccc34)n2)c(OC)cc1N(C)C12CC(CN(C)C)(C1)C2]

Step 1: 3-(2-chloropyrimidin-4-yl)-1-methyl-1H-indole was synthesized by following the same procedure as described in step 1 from Example 1 by reacting 1-methyl-1H-indole instead 1-(bicyclo[1.1.1]pentan-1-yl)-1H-indole to afford 3-(2-chloropyrimidin-4-yl)-1-methyl-1H-indole (15%). ¹H NMR (400 MHz, CDCl₃): δ 8.43 (d, J=5.2 Hz, 1H,), 8.31-8.30 (m, 1H), 7.92 (s, 1H), 7.46 (d, J=5.2 Hz, 1H,), 7.40-7.32 (m, 3H), 3.86 (s, 3H).

Step 2: To a solution of 3-(2-chloropyrimidin-4-yl)-1-methyl-1H-indole (50 mg, 0.205 mmol), and 4-fluoro-2-methoxy-5-nitroaniline (40 mg, 0.215 mmol) in isopropyl alcohol (10 mL) was added 4-methylbenzenesulfonic acid (45 mg, 0.261 mmol). The resulting mixture was heated at 105° C. for 2.5 h. The mixture was cooled to RT. The precipitate was collected by filtration, washed with 2-pentanol (50 mL), and dried under vacuum to afford N-(4-fluoro-2-methoxy-5-nitrophenyl)-4-(1-methyl-1H-indol-3-yl)pyrimidin-2-amine as a yellow solid (51 mg, 62%). LC/MS (ESI) m/z 394.1 $[M+H]^+$.

Step 3: To a solution of N-(4-fluoro-2-methoxy-5-nitrophenyl)-4-(1-methyl-1H-indol-3-yl)pyrimidin-2-amine (200 mg, 0.508 mmol) and diisopropylethylamine (0.328 mg, 2.54 mmol) in dimethyl sulfoxide (4 mL) was added 3-((dimethylamino)methyl)-N-methylbicyclo[1.1.1]pentan-1-amine (117 mg, 0.762 mmol). The mixture was heated at 100° C. for 24 h. The mixture was cooled to RT and diluted with dichloromethane and water. The organic layer was separated, dried over Na₂SO₄ and concentrated in vacuo. The crude product was purified by HPLC (10:90 to 80:20 0.1% HCO₂H (aq):MeCN) to afford N1-(3-((dimethylamino)methyl)bicyclo[1.1.1]pentan-1-yl)-5-methoxy-N1-methyl-N4-(4-(1-methyl-1H-indol-3-yl)pyrimidin-2-yl)-2-nitrobenzene-1,4-diamine (140 mg, 52%). LC/MS (ESI) m/z 528.6 $[M+H]^+$.

Step 4: To the solution of N1-(3-((dimethylamino)methyl)bicyclo[1.1.1]pentan-1-yl)-5-methoxy-N1-methyl-N4-(4-(1-methyl-1H-indol-3-yl)pyrimidin-2-yl)-2-nitrobenzene-1,4-diamine (50 mg, 0.095 mmol) in acetic acid (1 mL) under argon was added iron powder (27 mg, 0.475 mmol). The mixture was stirred at 50° C. for 1 h. The mixture was then cooled to RT and filtered to afford N1-(3-((dimethylamino)methyl)bicyclo[1.1.1]pentan-1-yl)-5-methoxy-N1-methyl-N4-(4-(1-methyl-1H-indol-3-yl)pyrimidin-2-yl)benzene-1,2,4-triamine as solution in acetic acid, which was used in the next step without further purification. LC/MS (ESI) m/z 498.7 $[M+H]^+$.

Step 5: To the solution of N1-(3-((dimethylamino)methyl)bicyclo[1.1.1]pentan-1-yl)-5-methoxy-N1-methyl-N4-(4-(1-methyl-1H-indol-3-yl)pyrimidin-2-yl)benzene-1,2,4-triamine in acetic acid (obtained from step 4) at 0° C. was added acryloyl chloride (8.59 mg, 0.095 mmol) in DCM (0.2 mL). After 15 min, the reaction mixture was diluted with ethyl acetate and water. The organic layer was separated, dried over Na₂SO₄, concentrated and purified by HPLC (10:90 to 80:20 0.1% HCO₂H (aq): MeCN) to afford N-(2-((3-((dimethylamino)methyl)bicyclo[1.1.1]pentan-1-yl)(methyl)amino)-4-methoxy-5-((4-(1-methyl-1H-indol-3-yl)pyrimidin-2-yl)amino)phenyl)acrylamide (20 mg, 42%). ¹H NMR (400 MHz, DMSO-d₆): δ 9.38 (s, 1H), 9.20 (s, 1H), 8.97 (s, 1H), 8.69 (s, 1H), 8.32 (d, J=5.6 Hz, 1H), 8.25 (m, 1H), 7.54 (d, J=8.4 Hz, 1H), 7.29-7.24 (m, 2H), 7.17 (t, J=7.2 Hz, 1H), 6.92 (s, 1H), 6.80-6.73 (m, 1H), 6.24 (dd, J=16.8, 1.6 Hz, 1H), 5.73 (d, J=10.0 Hz, 1H), 3.92 (s, 3H), 3.86 (s, 3H), 3.29 (d, J=4.8 Hz, 2H), 2.73 (s, 9H), 1.87 (s, 6H); LC/MS (ESI) m/z 552.6 $[M+H]^+$.

Example 5

N-(5-((4-(1-(bicyclo[1.1.1]pentan-1-yl)-1H-indazol-3-yl)pyrimidin-2-yl)amino)-2-((2-(dimethylamino)ethyl)(methyl)amino)-4-methoxyphenyl)acrylamide

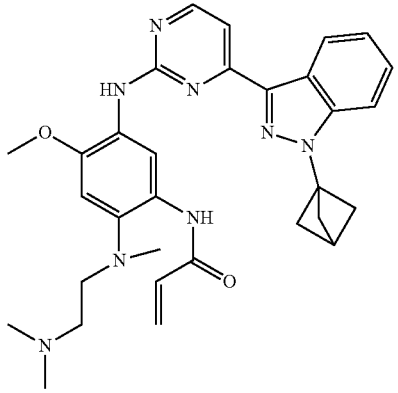 [SMILES: C=CC(=O)Nc1cc(Nc2nccc(-c3nn(C45CC(C4)C5)c4ccccc34)n2)c(OC)cc1N(C)CCN(C)C]

Step 1: Sodium hydride (60% dispersion in mineral oil, 598 mg, 14.94 mmol) was added to a stirring solution of 4-chloro-2-methylthiopyrimidine (1.45 mL, 12.45 mmol), 2-fluoro-benzaldehyde (1.57 mL, 14.94 mmol) and 1,3-dimethylimidazolium iodide (4.15 mmol). The resulting mixture was heated at reflux for 4 h. The mixture was cooled to RT, and then partitioned between ethyl acetate and water. The organic layer was separated, dried over $Na_2SO_4$, filtered and evaporated under reduced pressure. The crude residue was purified by column chromatography ($SiO_2$, hexanes/EtOAc) to afford (2-fluorophenyl)-(2-methylsulfanyl-pyrimidin-4-yl)-methanone as a pale yellow solid (2 g, 64%). LC/MS (ESI) m/z 249.2 [M+H]$^+$.

Step 2: At mixture of (2-Fluoro-phenyl)-(2-methylsulfanyl-pyrimidin-4-yl)-methanone (50 mg, 0.2 mmol), bicyclo[0.1.11]pentan-1-ylhydrazine (23.5 mg, 0.24 mmol) and cesium carbonate (282.25 mg, 0.8 mmol) in dimethyl acetamide (3 mL) was heated at 150° C. for 8 h. The mixture was then diluted with dichloromethane (50 mL) and washed with water (2×20 mL). The organic layer was separated, dried over $Na_2SO$ and concentrated. The residue was purified by HPLC (10:90 to 80:20 0.1% $HCO_2H$ (aq):MeCN) to afford 1-(bicyclo[L.1.1]pentan-1-yl)-3-(2-(methylthio)pyrimidin-4-yl)-1H-indazole as a red oil (30 mg. 0.097 mmol, 48%). LC/MS (ESI) m/z 309.4 [M+H]$^+$.

Step 3: To a solution of 1-(bicyclo[1.1.1]pentan-1-yl)-3-(2-(methylthio)pyrimidin-4-yl)-1H-indazole (1.2 g, 3.89 mmol) in dichloromethane (10 mL) was added 2-chlorobenzoic acid (1.21 g, 7.78 mmol). The mixture was stirred at RT overnight. The resulting suspension was filtered and washed with dichloromethane. The filtrate was concentrated to afford 1-(bicyclo[1.1.1]pentan-1-yl)-3-(2-(methylsulfonyl)pyrimidin-4-yl)-1H-indazole as a pale yellow solid (1.25 g, 3.68 mmol, 94%), which was used directly in the next step. LC/MS (ESI) m/z 341.4 [M+H]$^+$.

Step 4: To a solution of 1-(bicyclo[1.1.1]pentan-1-yl)-3-(2-(methylsulfonyl)pyrimidin-4-yl)-1H-indazole (340 mg, 1.0 mmol) and 4-Fluoro-2-methoxy-5-nitro-phenylamine (223.2 mg, 1.2 mmol) in anhydrous THF (5 mL) was added sodium hydride (60 mg, 1.5 mmol, 60% dispersion in mineral oil). The mixture was stirred at 60° C. overnight. The mixture was then diluted with water and extracted with DCM. The organic layer was dried over $Na_2SO_4$ and concentrated. The residue was purified by HPLC (10:90 to 80:20 0.1% $HCO_2H$ (aq): MeCN) to afford 4-(1-(bicyclo[1.1.1]pentan-1-yl)-1H-indazol-3-yl)-N-(4-fluoro-2-methoxy-5-nitrophenyl)pyrimidin-2-amine (98 mg, 0.22 mmol, 22%). LC/MS (ESI) m/z 447.5 [M+H]$^+$.

Step 5: To a solution of 4-(1-(bicyclo[1.1.1]pentan-1-yl)-1H-indazol-3-yl)-N-(4-fluoro-2-methoxy-5-nitrophenyl)pyrimidin-2-amine (100 mg, 0.224 mmol) in dimethyl acetamide (3 mL) was added $N^1,N^1,N^2$-trimethylethane-1,2-diamine (45.7 mg, 0.448 mmol). The mixture was stirred at 100° C. for 2 h and then cooled to RT. The mixture was diluted with water and extracted with dichloromethane (2×50 mL). The combined organic layers were dried over $Na_2SO_4$ and concentrated. The residue was purified by HPLC (10:90 to 80:20 0.1% $HCO_2H$ (aq): MeCN) to afford N1-(4-(1-(bicyclo[1.1.1]pentan-1-yl)-1H-indazol-3-yl)pyrimidin-2-yl)-N4-(2-(dimethylamino)ethyl)-2-methoxy-N4-methyl-5-nitrobenzene-1,4-diamine (60 mg, 0.114 mmol, 50%). LC/MS (ESI) m/z 529.3 [M+H]$^+$.

Step 6: To a solution of N1-(4-(1-(bicyclo[1.1.1]pentan-1-yl)-1H-indazol-3-yl)pyrimidin-2-yl)-N4-(2-(dimethylamino)ethyl)-2-methoxy-N4-methyl-5-nitrobenzene-1,4-diamine (60 mg, 0.114 mmol) in acetic acid (2 mL) under Ar, was added Iron powder (31 mg, 0.57 mmol). The mixture was stirred at 60° C. for 1 h. The mixture was then cooled to RT and filtered. It was used directly as a solution of N4-(4-(1-(bicyclo[1.1.1]pentan-1-yl)-1H-indazol-3-yl)pyrimidin-2-yl)-N1-(2-(dimethylamino)ethyl)-5-methoxy-N1-methylbenzene-1,2,4-triamine in acetic acid. LC/MS (ESI) m/z 499.7 [M+H]$^+$.

Step 7: To a solution of N4-(4-(1-(bicyclo[1.1.1]pentan-1-yl)-1H-indazol-3-yl)pyrimidin-2-yl)-N1-(2-(dimethylamino)ethyl)-5-methoxy-N1-methylbenzene-1,2,4-triamine in acetic acid obtained in step 6 (Example 5), was added acryloyl chloride (12.32 mg, 0.137 mmol) in dichloromethane (0.2 mL). The mixture was stirred at RT for 15 mins. The mixture was then filtered, and the filtrate was concentrated. The residue was purified by HPLC (10:90 to 80:20 0.1% $HCO_2H$ (aq):MeCN) to afford N-(5-((4-(1-(bicyclo[1.1.1]pentan-1-yl)-1H-indazol-3-yl)pyrimidin-2-yl)amino)-2-((2-(dimethylamino)ethyl)(methyl)amino)-4-methoxyphenyl)acrylamide as a brownish solid (20 mg, 0.036 mmol, 31% over two steps). $^1$H NMR (400 MHz, DMSO-$d_6$): δ 9.61 (s, 1H), 8.58 (s, 1H), 8.47-8.44 (m, 2H), 8.34 (s, 1H), 7.83 (d, J=8.4 Hz, 1H), 7.46-7.43 (m, 2H), 7.21-7.18 (m, 1H), 7.02 (s, 1H), 6.68-6.60 (m, 1H), 6.28 (d, J=16.8 Hz, 1H), 5.78 (d, J=10.0 Hz, 1H), 3.86 (s, 3H), 3.33-3.27 (m, 4H), 2.82-2.81 (m, 6H), 2.76 (s, 1H), 2.52 (s, 3H), 2.51 (s, 6H); LC/MS (ESI) m/z 553.4 [M+H]$^+$.

Example 6

N-(2-((3-(dimethylamino)bicyclo[1.1.1]pentan-1-yl)(methyl)amino)-4-methoxy-5-((4-(1-methyl-1H-indol-3-yl)pyrimidin-2-yl)amino)phenyl)acrylamide

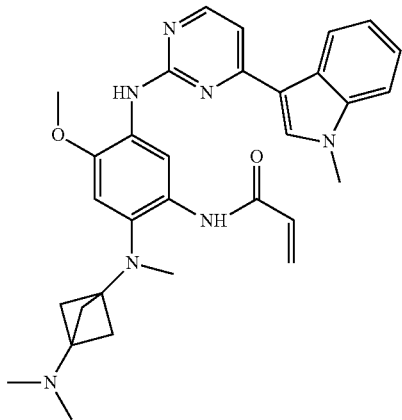 [SMILES: C=CC(=O)Nc1cc(Nc2nccc(-c3cn(C)c4ccccc34)n2)c(OC)cc1N(C)C12CC(N(C)C)(C1)C2]

Step 1: To a stirred suspension of 2,4-dichloropyrimidine (2.637 g, 20.13 mmol) in dimethoxyethane (30 mL) was added aluminum trichloride (2.67 g, 20.134 mmol) at 10° C. The mixture was stirred at 10° C. for 15 mins. 1-methyl-1H-indole (3.0 g, 20.13 mmol) was added, and the mixture was heated under reflux for 2 h. The mixture was cooled to RT, poured into water (30 mL) and extracted with ethyl acetate (3×50 mL). The combined organic layers were washed with water (30 mL) and brine (30 mL), dried over sodium sulphate and concentrated to afford 3-(2-chloropyrimidin-4-yl)-1-methyl-1H-indole (3.0 g, 12.34 mmol, 61%). LC/MS (ESI) m/z 244.3 [M+H]$^+$.

Step 2: To a stirred solution of 3-(2-chloropyrimidin-4-yl)-1-methyl-1H-indole (4 g, 16.46 mmol) in 2-pentanone (40 mL) was added 4-fluoro-2-methoxy-5-nitroaniline (3.06 g, 16.46 mmol) and p-toluenesulfonic acid (0.312 g, 1.65 mmol). The mixture was heated to 80° C. After 16 h, the mixture cooled to RT and diluted with water (40 mL). The resulting solid was filtered and dried to afford N-(4-fluoro-2-methoxy-5-nitrophenyl)-4-(1-methyl-1H-indol-3-yl)pyrimidin-2-amine (4.0 g, 10.18 mmol, 62%). LC/MS (ESI) m/z 394.20 [M+H]$^+$.

Step 3: To a stirred solution of N-(4-fluoro-2-methoxy-5-nitrophenyl)-4-(1-methyl-1H-indol-3-yl)pyrimidin-2-amine (1.0 g, 2.54 mmol) in dimethyl sulfoxide (50 mL) was added N1,N1,N3-trimethylbicyclo[1.1.1]pentane-1,3-diamine hydrochloride (0.537 g, 3.05 mmol, intermediate 1, Step-10) and potassium carbonate (0.701 g, 5.08 mmol). The mixture was heated at 65° C. for 16 h. The mixture was then cooled to RT, poured into water (20 mL) and extracted with ethyl acetate (3×50 mL). The combined organic layers were washed with water (20 mL) and brine (20 mL), dried over sodium sulphate and concentrated to afford N1-(5-methoxy-4-(4-(1-methyl-1H-indol-3-yl)pyrimidin-2-ylamino)-2-nitrophenyl)-N1,N3,N3-trimethylbicyclo[1.1.1]pentane-1,3-diamine (0.420 g, 0.818 mmol, 32%). LC/MS (ESI) m/z 514.1 [M+H]$^+$.

Step 4: To a stirred solution N1-(5-methoxy-4-(4-(1-methyl-1H-indol-3-yl)pyrimidin-2-ylamino)-2-nitrophenyl)-N1,N3,N3-trimethylbicyclo[1.1.1]pentane-1,3-diamine (0.400 g, 0.779 mmol) in ethyl acetate:tetrahydrofuran (10 mL) was added 10% wet Pd/C (100 mg). The reaction was stirred at RT under hydrogen atmosphere (60 psi) for 6 h. The mixture was filtered through celite, and the organic fractions were concentrated to afford N1-(3-(dimethylamino)bicyclo[1.1.1]pentan-1-yl)-5-methoxy-N1-methyl-N4-(4-(1-methyl-1H-indol-3-yl)pyrimidin-2-yl)benzene-1,2,4-triamine (260 g, 0.538 mmol, 69%). LC/MS (ESI) m/z 484.1 [M+H]$^+$.

Step 5: To a stirred suspension of N1-(3-(dimethylamino)bicyclo[1.1.1]pentan-1-yl)-5-methoxy-N1-methyl-N4-(4-(1-methyl-1H-indol-3-yl)pyrimidin-2-yl)benzene-1,2,4-triamine (0.270 g, 0.559 mmol) in tetrahydrofuran:water (25 mL) was added 3-chloropropanoyl chloride (7.10 mg, 0.559 mmol). The reaction was stirred at 5° C. for 15 mins. To this mixture was added sodium hydroxide (89.0 mg, 2.236 mmol), and the mixture was stirred at RT for 16 h. The mixture was poured into water (5 mL) and extracted with ethyl acetate (3×30 mL). The combined organic layers were washed with water (10 mL) and brine (10 mL), dried over sodium sulphate and concentrated to afford N-(2-((3-(dimethylamino)bicyclo[1.1.1]pentan-1-yl)(methyl)amino)-4-methoxy-5-((4-(1-methyl-1H-indol-3-yl)pyrimidin-2-yl)amino)phenyl)acrylamide (0.110 g, 0.204 mmol, 37%). $^1$H NMR (300 MHz, CDCl$_3$) δ 9.86 (s, 1H), 9.07 (s, 1H), 8.78 (s, 1H), 8.38 (d, J=5.6 Hz, 1H), 8.14-8.04 (m, 2H), 7.81 (s, 1H), 7.40 (d, J=7.2 Hz, 1H), 7.28-7.26 (m, 1H), 7.22 (d, J=5.2 Hz, 1H), 6.71 (s, 1H), 6.45-6.37 (m, 2H), 5.77 (dd, J=7.2, 2.0 Hz, 1H), 4.0 (s, 3H), 3.88 (s, 3H), 2.70 (s, 3H), 2.27 (s, 6H), 1.82 (s, 6H); LC/MS (ESI) m/z 538.5 [M+H]$^+$.

Intermediate 6

1-(3-fluorobicyclo[1.1.1]pentan-1-yl)-1H-indole

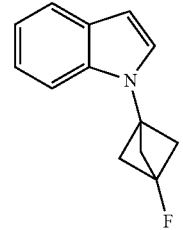 [SMILES: FC12CC(n3ccc4ccccc43)(C1)C2]

Step 1: To a solution of 2-(2-bromophenyl)acetic acid (2.0 g, 9.30 mmol) in CH$_2$Cl$_2$ (40 mL) at 0° C. was added Hunig's base (4.8 mL, 27.90 mmol), N1-((ethylimino)methylene)-N3,N3-dimethylpropane-1,3-diamine (2.67 g, 13.95 mmol) and HOBt (2.1 g, 13.90 mmol) followed by bicyclo[1.1.1]pentan-1-amine hydrochloride (1.52 g, 11.16 mmol). The mixture was stirred at RT for 16 h. After the completion of the reaction, the mixture was concentrated under reduced pressure to afford a residue that was purified by chromatography on SiO$_2$ (100-200 mesh, eluent: 15% ethyl acetate in petroleum ether) to afford of 2-(2-bromophenyl)-N-(3-fluorobicyclo[1.1.1]pentan-1-yl)acetamide as a white solid (1.2 g, 43%). MS (ESI) m/z 298.11 [M+H]$^+$.

Step 2: To a flame dried vial with stir bar was added 2-(2-bromophenyl)-N-(3-fluorobicyclo[1.1.1]pentan-1-yl)acetamide (0.85 g, 2.86 mmol), followed by Pd(OAc)$_2$ (0.19 g, 0.28 mmol), tri-tert-butylphosphonium tetrafluoroborate (0.16 g, 0.57 mmol) and Cs$_2$CO$_3$ (1.39 g, 4.29 mmol). The reaction vial was purged with argon. Degassed toluene (30 mL) was added, and the mixture was heated at 100° C. for 4 h. After the reaction completed (TLC), the mixture was filtered through a pad of celite and washed with EtOAc (30 mL). The filtrate was concentrated under reduced pressure to afford a residue that was purified by chromatography on SiO$_2$ (100-200 mesh, eluent: 5% ethyl acetate in petroleum ether) to afford 1-(3-fluorobicyclo[1.1.1]pentan-1-yl)indolin-2-one as an off-white solid (0.37 g, 60%). MS (ESI) m/z 218.32 [M+H]$^+$.

Step 3: To a solution of 1-(bicyclo[1.1.1]pentan-1-yl) indolin-2-one (0.5 g, 2.48 mmol) in THF (10 mL) at −78° C. was added DIBAL-H (1M toluene, 6.2 mL, 6.21 mmol) dropwise. The mixture was stirred at −78° C. for 2 h. After the completion of the reaction (TLC), the mixture was cooled to 0° C., and the reaction was quenched with MeOH (10 mL). The mixture was filtered through a pad of celite, washed with EtOAc (30 mL), dried over Na$_2$SO$_4$ and concentrated under reduced pressure. The resulting residue was purified by chromatography on SiO$_2$ (100-200 mesh, eluent: 2% ethyl acetate in petroleum ether) to afford 1-(3-fluorobicyclo[1.1.1]pentan-1-yl)-1H-indole as a pale yellow liquid (0.27 g, 58%). $^1$H NMR (400 MHz, CDCl$_3$) δ 7.61 (d, J=7.6 Hz, 1H), 7.42 (d, J=7.6 Hz, 1H), 7.21 (t, J=8.0 Hz, 1H), 7.13 (t, J=8.0 Hz, 1H), 6.98 (d, J=3.6 Hz, 1H), 6.50 (d, J=3.6 Hz, 1H), 2.73 (s, 6H); MS (ESI) m/z 202.1 [M+H]$^+$.

Example 7

N-(2-((2-(dimethylamino)ethyl)(methyl)amino)-5-((4-(1-(3-fluorobicyclo[1.1.1]pentan-1-yl)-1H-indol-3-yl)pyrimidin-2-yl)amino)-4-methoxyphenyl)acrylamide

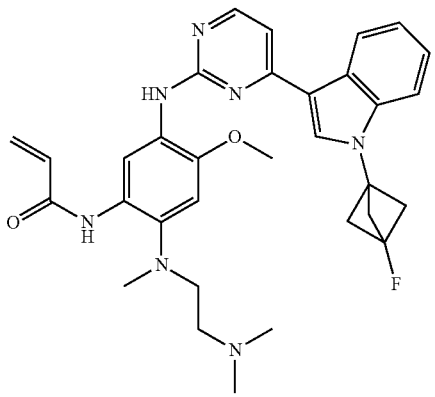 [SMILES: C=CC(=O)Nc1cc(Nc2nccc(-c3cn(C45CC(F)(C4)C5)c4ccccc34)n2)c(OC)cc1N(C)CCN(C)C]

Step 1: To a stirred solution of 1-(3-fluorobicyclo[1.1.1] pentan-1-yl)-1H-indole (100 mg, 0.49 mmol) in DME (1.6 mL) at RT was added 2,4-dichloropyrimidine (74 mg, 0.49 mmol) followed by AlCl$_3$ (99 mg, 0.74 mmol). The mixture was stirred at 80° C. for 16 h. After completion of reaction (TLC), the mixture was diluted with dichloromethane (5 mL), washed with water followed by brine, dried over Na$_2$SO$_4$ and concentrated under reduced pressure. The residue was purified by chromatography on SiO$_2$ (100-200 mesh, eluent: 10% ethyl acetate in petroleum ether) to afford 3-(2-chloropyrimidin-4-yl)-1-(3-fluorobicyclo[1.1.1]pentan-1-yl)-1H-indole as a yellow solid (80 mg, 51%). MS (ESI) m/z 313.92 [M+H]$^+$.

Step 2: To a stirred solution of 3-(2-chloropyrimidin-4-yl)-1-(3-fluorobicyclo[1.1.1]pentan-1-yl)-1H-indole (180 mg, 0.57 mmol) in 2-pentanol (8 mL) at RT was added 4-fluoro-2-methoxy-5-nitroaniline (107 mg, 0.57 mmol) and PTSA (10 mg, 0.05 mmol). The mixture was stirred at 80° C. for 16 h. After completion of reaction, the mixture was diluted with EtOAc (5 mL), washed with H$_2$O (2×5 mL) and brine (5 mL), dried over Na$_2$SO$_4$ and concentrated under reduced pressure. The residue was purified by chromatography on SiO$_2$ (100-200 mesh, eluent: 20% ethyl acetate in petroleum) to afford N-(4-fluoro-2-methoxy-5-nitrophenyl)-4-(1-(3-fluorobicyclo[1.1.1]pentan-1-yl)-1H-indol-3-yl)pyrimidin-2-amine as a dark green color solid (160 mg, 60%). MS (ESI) m/z 464.01 [M+H]$^+$.

Step 3: To a stirred solution of N-(4-fluoro-2-methoxy-5-nitrophenyl)-4-(1-(3-fluorobicyclo[1.1.1]pentan-1-yl)-1H-indol-3-yl)pyrimidin-2-amine (160 mg, 0.34 mmol) in DMA (6 mL) at RT was added N1,N1,N2-trimethylethane-1,2-diamine (0.06 mL, 0.51 mmol) followed by DIPEA (0.08 mL, 0.44 mmol). The mixture was stirred at 85° C. for 5 h. After completion of reaction, the mixture was diluted with EtOAc (10 mL), washed with ice cold H$_2$O (10 mL) and brine (5 mL), dried over Na$_2$SO$_4$ and concentrated. The residue was purified by chromatography on SiO$_2$ (100-200 mesh, eluent: 5% methanol in dichloromethane) to afford 160 mg (85%) of N-(4-fluoro-2-methoxy-5-nitrophenyl)-4-(1-(3-fluorobicyclo[1.1.1]pentan-1-yl)-1H-indol-3-yl)pyrimidin-2-amine as a bright red solid. MS (ESI) m/z 546.09 [M+H]$^+$.

Step 4: To a stirred solution of N1-(2-(dimethylamino) ethyl)-N4-(4-(1-(3-fluorobicyclo[1.1.1]pentan-1-yl)-1H-indol-3-yl)pyrimidin-2-yl)-5-methoxy-N1-methyl-2-nitrobenzene-1,4-diamine (160 mg, 0.294 mmol) in THF:EtOAc (1:1, 10 mL) was added Pd/C (10% w/w, wet, 80 mg). The mixture was stirred at RT under H$_2$ (1 atm) for 2 h. After the completion of the reaction, the mixture was filtered through a pad of celite, washed with EtOAc (50 mL) and concentrated under reduced pressure. The residue was purified by chromatography on SiO$_2$ (100-200 mesh, eluent: 15% methanol in dichloromethane) to afford N1-(2-(dimethylamino)ethyl)-N4-(4-(1-(3-fluorobicyclo[1.1.1]pentan-1-yl)-1H-indol-3-yl)pyrimidin-2-yl)-5-methoxy-N1-methylbenzene-1,2,4-triamine as a pale brown solid (140 mg, 92%). MS (ESI) m/z 516.43 [M+H]$^+$.

Step 5: To a stirred solution of N1-(2-(dimethylamino) ethyl)-N4-(4-(1-(3-fluorobicyclo[1.1.1]pentan-1-yl)-1H-indol-3-yl)pyrimidin-2-yl)-5-methoxy-N1-methylbenzene-1,2,4-triamine (140 mg, 0.26 mmol) in THF (10 mL) was added DIPEA (0.14 mL, 0.89 mmol) followed by acryloyl chloride (0.02 mL, 0.26 mmol). The mixture was stirred at 0° C. for 10 mins. Upon the completion of reaction, the reaction was quenched with water (30 mL) and extracted with EtOAc (3×20 mL). The combined organic layers were washed with water (10 mL) and brine (10 mL), dried over Na$_2$SO$_4$ and concentrated under reduced pressure. The residue was purified by a reverse phase HPLC using acetonitrile (contains 0.05% formic acid) in water (contains 0.05% formic acid) to afford N-(2-((2-(dimethylamino)ethyl) (methyl)amino)-5-((4-(1-(3-fluorobicyclo[1.1.1]pentan-1-yl)-1H-indol-3-yl)pyrimidin-2-yl)amino)-4-methoxyphenyl)acrylamide as an off-white solid (13 mg, 8.4%). $^1$H NMR (300 MHz, DMSO-d$_6$) δ 10.14 (s, 1H), 8.87 (s, 1H), 8.39-8.30 (m, 2H), 8.27 (s, 1H), 8.04 (s, 1H), 7.66 (d, J=7.8 Hz, 1H), 7.28 (d, J=5.4 Hz, 1H), 7.24 (d, J=7.5 Hz, 1H), 7.13 (t, J=7.5 Hz, 1H), 7.03 (s, 1H), 6.41 (dd, J=16.8, 10.2 Hz, 1H), 6.19 (dd, J=16.8, 2.0 Hz, 1H), 5.74 (dd, J=10.2, 2.0 Hz, 1H), 3.82 (s, 3H), 2.94-2.81 (m, 8H), 2.73 (s, 3H), 2.36-2.26 (m, 2H), 2.21 (s, 6H); MS (ESI) m/z 570.43 [M+H]$^+$.

Example 8

N-(5-((4-(1-(Bicyclo[1.1.1]pentan-1-yl)-1H-indol-3-yl)pyrimidin-2-yl)amino)-4-methoxy-2-(methyl(2-(methylamino)ethyl)amino)phenyl)acrylamide

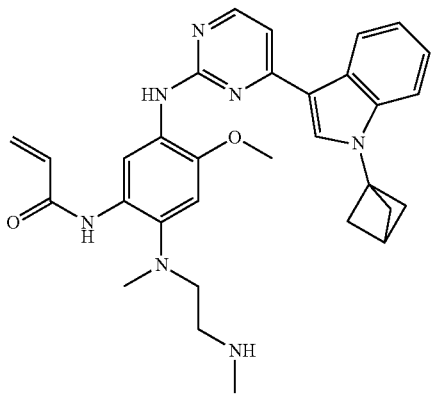 [SMILES: C=CC(=O)Nc1cc(Nc2nccc(-c3cn(C45CC(C4)C5)c4ccccc34)n2)c(OC)cc1N(C)CCNC]

Step 1: To a stirred solution of 4-(1-(bicyclo[1.1.1]pentan-1-yl)-1H-indol-3-yl)-N-(4-fluoro-2-methoxy-5-nitrophenyl)pyrimidin-2-amine (3.0 g, 6.73 mmol) in DMA (100 mL) were added N1,N2-dimethylethane-1,2-diamine (1.09 mL, 10.09 mmol) and DIPEA (1.45 mL, 8.75 mmol) at RT. After being stirred at 85° C. for 5 h, the mixture was diluted with EtOAc (300 mL), washed with ice cold $H_2O$ (100 mL) and brine (50 mL), dried over $Na_2SO_4$, and concentrated under reduced pressure. The residue was purified by chromatography on $SiO_2$ (100-200 mesh, eluent: 5% methanol in $CH_2Cl_2$) to afford N1-(4-(1-(bicyclo[1.1.1]pentan-1-yl)-1H-indol-3-yl)pyrimidin-2-yl)-2-methoxy-N4-methyl-N4-(2-(methylamino)ethyl)-5-nitrobenzene-1,4-diamine (1.9 g, 55%) as a bright red solid. MS (ESI) m/z 514.14 $[M+H]^+$.

Step 2: To a stirred solution of N1-(4-(1-(bicyclo[1.1.1]pentan-1-yl)-1H-indol-3-yl)pyrimidin-2-yl)-2-methoxy-N4-methyl-N4-(2-(methylamino)ethyl)-5-nitrobenzene-1,4-diamine (1.9 g, 3.69 mmol) in THF (50 mL) were added $Et_3N$ (1.56 mL, 11.08 mmol), $(Boc)_2O$ (0.85 mL, 3.69 mmol) and DMAP (45 mg, 0.36 mmol). After being stirred at 70° C. for 8 h, the mixture was cooled to RT, diluted with EtOAc (100 mL), washed with $H_2O$ (25 mL) and brine (25 mL), dried over $Na_2SO_4$, and concentrated. The residue was purified by chromatography on $SiO_2$ (100-200 mesh, eluent: 5% methanol in $CH_2Cl_2$) to afford tert-butyl (2-((4-((4-(1-(bicyclo[1.1.1]pentan-1-yl)-1H-indol-3-yl)pyrimidin-2-yl)amino)-5-methoxy-2-nitrophenyl)(methyl)amino)ethyl)(methyl)carbamate (1.4 g, 61%) as a pale yellow solid. MS (ESI) m/z 614.10 $[M+H]^+$.

Step 3: To a stirred solution of tert-butyl (2-((4-((4-(1-(bicyclo[1.1.1]pentan-1-yl)-1H-indol-3-yl)pyrimidin-2-yl)amino)-5-methoxy-2-nitrophenyl)(methyl)amino)ethyl)(methyl) carbamate (1.4 g, 2.28 mmol) in THF:EtOAc (1:1 ratio, 40 mL) was added Pd/C (10% w/w, wet, 400 mg). After being stirred at RT under $H_2$ (1 atm) for 8 h, the mixture was filtered through a pad of celite, washed with EtOAc (100 mL) and concentrated under reduced pressure. The residue was purified by chromatography on $SiO_2$ (100-200 mesh, eluent: 15% methanol in dichloromethane) to afford tert-butyl(2-((2-amino-4-((4-(1-(bicyclo[1.1.1]pentan-1-yl)-1H-indol-3-yl)pyrimidin-2-yl)amino)-5-methoxyphenyl)(methyl) amino)ethyl)(methyl)carbamate (1.0 g, 75%) as a pale yellow solid. MS (ESI) m/z 584.08 $[M+H]^+$.

Step 4: To a stirred solution of tert-butyl (2-((2-amino-4-((4-(1-(bicyclo[1.1.1]pentan-1-yl)-1H-indol-3-yl)pyrimidin-2-yl)amino)-5-methoxyphenyl)(methyl)amino)ethyl)(methyl) carbamate (400 mg, 0.68 mmol) in THF (100 mL) were added DIPEA (0.36 mL, 2.05 mmol) and acryloyl chloride (0.044 mL, 0.54 mmol). After being stirred at 0° C. for 10 min, the reaction was quenched by water (50 mL) and the mixture was extracted with EtOAc (5×20 mL). The combined organic layers were washed with water (30 mL) and brine (50 mL), dried over $Na_2SO_4$, and concentrated under reduced pressure. The residue was purified by chromatography (Grace-normal phase, eluent: 10% methanol in $CH_2Cl_2$) to afford tert-butyl (2-((2-acrylamido-4-((4-(1-(bicyclo[1.1.1]pentan-1-yl)-1H-indol-3-yl)pyrimidin-2-yl)amino)-5-methoxyphenyl)(methyl)amino)ethyl)(methyl) carbamate (360 mg, 82%) as an off-white solid. MS (ESI) m/z 638.11 $[M+H]^+$.

Step 5: To a stirred solution of tert-butyl (2-((2-acrylamido-4-((4-(1-(bicyclo[1.1.1]pentan-1-yl)-1H-indol-3-yl)pyrimidin-2-yl)amino)-5-methoxyphenyl)(methyl) amino)ethyl)(methyl)carbamate (260 mg, 0.407 mmol) in $CH_2Cl_2$ (5 mL) was added TFA (0.3 mL, 4.07 mmol) at 0° C. After being stirred at 0° C. for 1 h, the reaction was quenched by sat. aq. $NaHCO_3$ solution (5 mL) and the mixture was extracted with $CH_3OH:CH_2Cl_2$ (10:1 ratio, 3×10 mL). The combined organic layers were washed with water (10 mL) and brine (10 mL), dried over $Na_2SO_4$, and concentrated under reduced pressure. The residue was purified by preparative HPLC [Mobile phase: (A) Water contains 0.1% Formic acid (B) Acetonitrile contains 0.1% Formic acid Flow: 19 mL/min Gradient—(T/% B):0/10,0.1/25,11/25, 11.1/98,13/98,13.1/10,15/10 Solubility:ACN+$H_2O$+THF Column used: Symmetry C18 (300×19) mm 7 u] to afford N-(5-((4-(1-(bicyclo[1.1.1]pentan-1-yl)-1H-indol-3-yl)pyrimidin-2-yl)amino)-4-methoxy-2-(methyl(2-(methylamino)ethyl)amino)phenyl) acrylamide (51 mg, 23%) as an off-white solid. $^1H$ NMR (300 MHz, DMSO-$d_6$) δ 10.12 (s, 1H), 8.8 (s, 1H), 8.4-8.2 (m, 4H), 8.02 (s, 1H), 7.68 (d, J=8.1 Hz, 1H), 7.28 (d, J=5.4 Hz, 1H), 7.21 (t, J=7.2 Hz, 1H), 7.11 (t, J=7.2 Hz, 1H), 6.96 (s, 1H), 6.7-6.58 (m, 1H), 6.19 (d, J=16.2 Hz, 1H), 5.71 (d, J=12.0 Hz, 1H), 3.83 (s, 3H), 3.02-2.94 (m, 2H), 2.8-2.72 (m, 2H), 2.71 (s, 1H), 2.67 (s, 3H), 2.45 (s, 6H), 2.42 (s, 3H). MS (ESI) m/z 538.17 $[M+H]^+$.

General methods and conditions for preparing compounds of Formula (I), or a pharmaceutically acceptable salt thereof, are described herein. Additional compounds of Formula (I), or a pharmaceutically acceptable salt thereof, that can be prepared using one of more of methods described herein include the following:

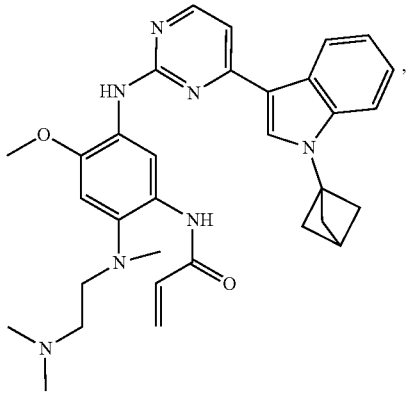

57
-continued
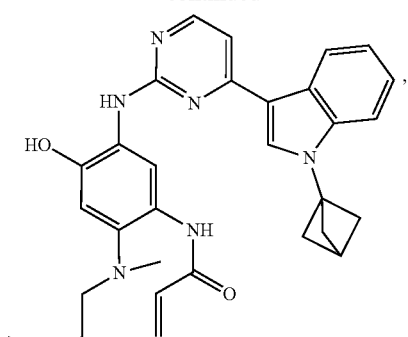
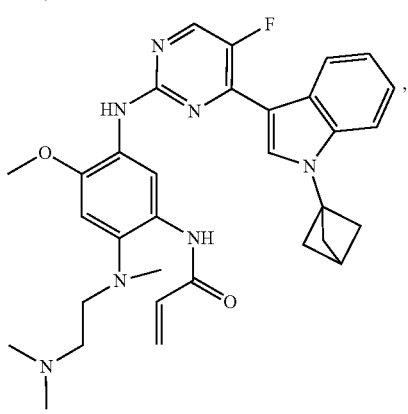
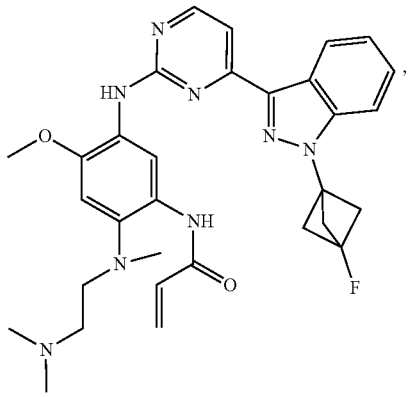
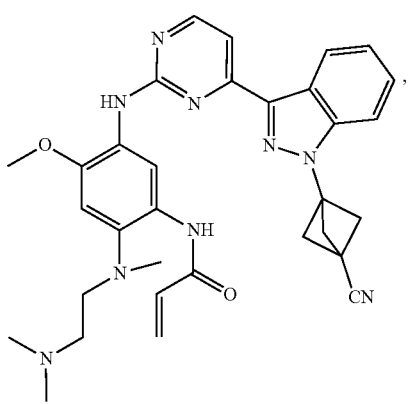
58
-continued
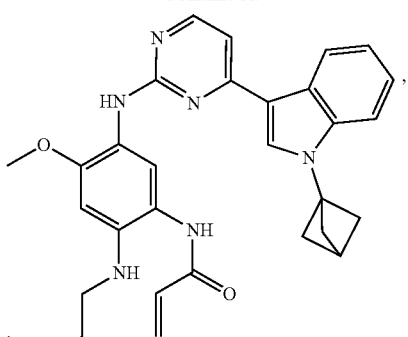
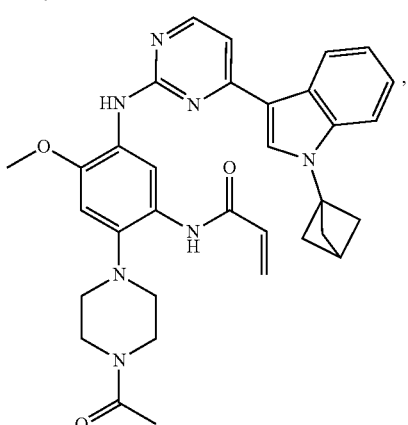
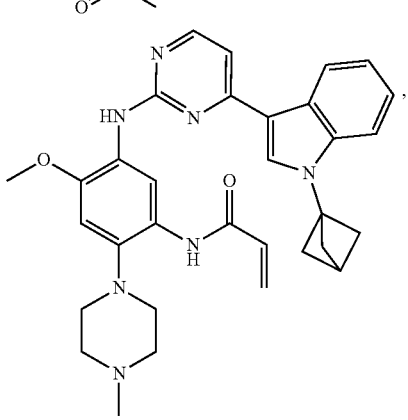
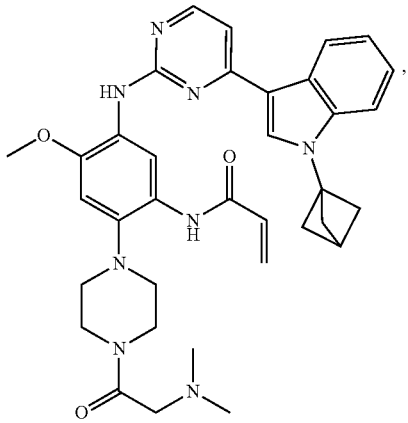

-continued

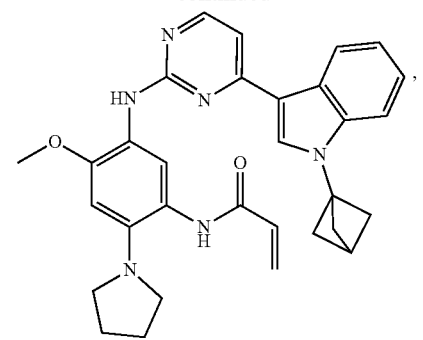

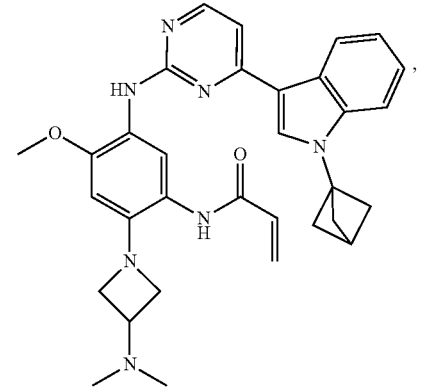

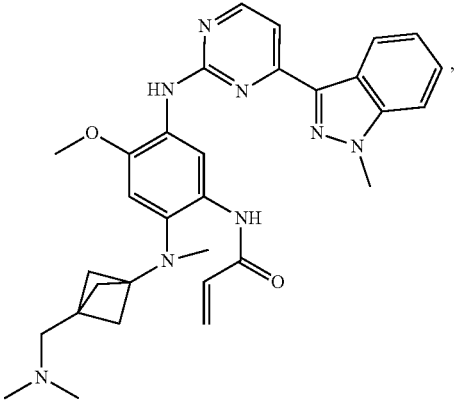

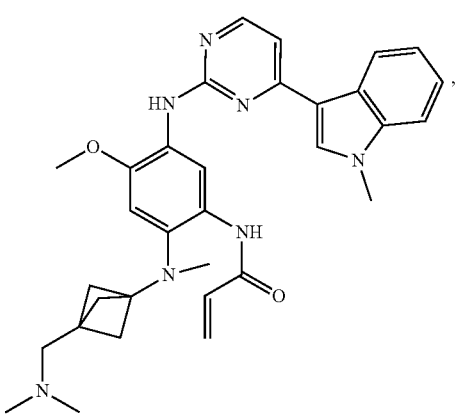

-continued

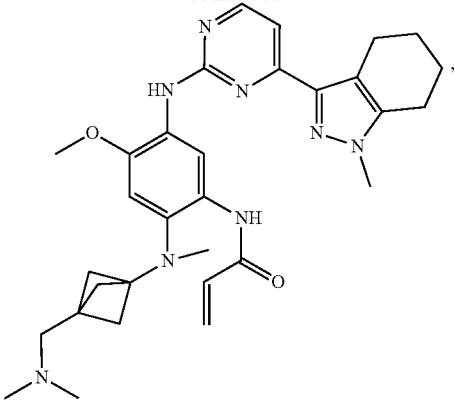

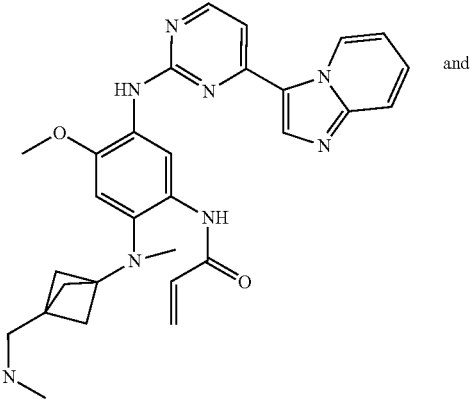

and

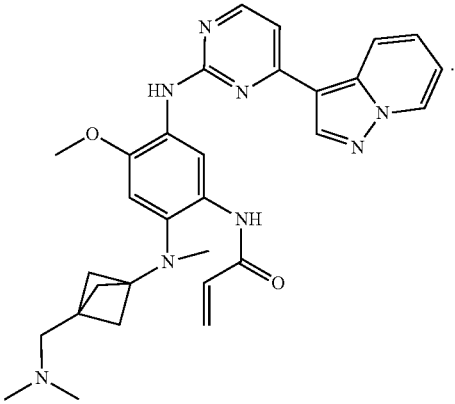

Example A

EGFR Biochemical Enzyme Assay Protocol

The inhibitory activity of a compound against EGFR (T790M/L858R) were determined with CisBio HTRF (homogenous time-resolved fluorescence) KinEASE TK (#62TKOPEC). The enzyme reaction contained recombinant N-terminal GST-tagged human EGFR (T790M/L858R), which phosphorylates the HTRF tyrosine kinase biotinylated substrate.

The sequence of the substrate is proprietary to CisBio. Test compounds were serially diluted in 100% (v/v) DMSO before being acoustically dispensed from an Echo 555 (Labcyte) into black Corning 1536-well assay plates. Kinase activity assays were performed in a total reaction volume of 3 μL per well. A 1.5 μL enzyme reaction consisted of 1.6 nM EGFR (T970M, L858R), 1 mM DTT, and 10 mM $MgCl_2$. A 1.5 µL substrate mix consisted of 1 µM TK substrate, 30 µM ATP, 1 mM DTT, and 10 mM MgCl$_2$. Following a 50 mins incubation, 3 µL of stop mix was added, which consisted of 250 nM Strep-XL665 and TK Ab-Cryptate diluted in kit detection buffer. The plates were incubated for 1 h before being read on Pherastar using standard HTRF settings. N-terminal GST-tagged recombinant human EGF receptor, with amino acids 696-end containing the T790M and L858R mutations, was obtained from Millipore.

Compounds of Formula (I) are active in this assay as provided in Table 1, where A=IC$_{50}$≤10 nM; B=IC$_{50}$>10 nM and <100 nM; and C=IC$_{50}$≥100 nM.

TABLE 1

| Example # | T790M/L858R (nM) | L858R (nM) | Del-19 (nM) | Wt (nM) | IGF1R (nM) | INSR (nM) |
|---|---|---|---|---|---|---|
| 1 | A | A | A | A | C | C |
| 2 | A | — | A | A | C | C |
| 3 | A | — | A | A | C | C |
| 4 | C | — | C | B | C | C |
| 5 | A | — | A | A | C | C |
| 6 | A | C | C | C | C | C |
| 7 | A | A | A | A | — | — |
| 8 | A | — | A | B | C | C |

Example B p-EGFR: Target Engagement Assay (Cell-Based Phospho-EGFR Assay) Western Blot Cell lines used as follows: A431 (WT), H1975 (L858R/T790M), PC9 (E746-A750 deletion): cells are grown in 12-well plates to 90% confluence and then incubated in low-serum (0.1% FBS) media for 16-18 h. Cells are then treated with varying concentration of test compounds (5, 1.25, 0.31, 0.078, 0.020 µM) or 0.5% DMSO in low-serum (0.1% FBS) media for 1 h. A431 cells are then stimulated with 50 ng/mL EGF for 15 mins. After treatment, cell monolayers are washed with cold PBS and immediately lysed by scraping into 50 µL cold Cell Extraction Buffer supplemented with Complete Protease inhibitors and phosphatase inhibitors. Lysate protein concentrations are determined by BCA assay and approximately 50 µg of each lysate were separated by 4-12% gradient SDS-PAGE transferred to nitrocellulose membrane and probed with specific antibodies. Phosphoprotein signals are visualized by western blot detection system or quantitated using Odyssey Infrared Imaging (Li-Cor Biosciences, Lincoln, Nebr.). To assess phospho-signaling, blots are immunoblotted with phospho and total antibodies for EGFR (Y1068), AKT, pS6RP and Erk1/2. Phospho-signals are normalized to total protein expression for each biomarker. Results are indicated as % DMSO control. Normalized data are fitted using a sigmoidal curve analysis program (Graph Pad Prism version 5) with variable Hill slope to determine the EC$_{50}$ values.

Antibodies: All primary antibodies are obtained from Cell Signaling (Danvers, MA) and used at 1:1000. Secondary antibodies are used at 1:20,000. Goat anti-mouse IgG IRDye 800CW antibody is obtained from LiCor Biosciences (Lincoln, NE) and goat anti-rabbit IgG Alexa Fluor 680 is obtained from Invitrogen (Carlsbad, CA).

Example C

EGFR Cell Proliferation Assays

Cell Lines: A431 (WT), H1975 (L858R/T790M), PC9 (E746-A750 deletion): A431 cells were grown in DMEM (Invitrogen, Carlsbad, CA) supplemented with 10% FBS (HyClone, South Logan, UT) and 1% Penicillin-Streptomycin (P/S, Lonza, Walkersville, MD). H1975 cells were grown in RPMI 1640 (Invitrogen) supplemented with 10% FBS and 1% P/S. Culture Collection (Manassas, Va.), and PC-9 cells were obtained from Japan. All cells were maintained and propagated as monolayer cultures at 37° C. in a humidified 5% CO$_2$ incubator. All cells were cultured according to recommendations.

In order to profile the effect of EGFR inhibitors in various tumorigenic cell lines, the cell lines were tested in the cell proliferation assay that exhibit different EGFR mutation status. Cell proliferation was measured using the CellTiter-Glo® Luminescent Cell Viability Assay. The assay involved the addition of a single reagent (CellTiter-Glo® Reagent) directly to cells cultured in serum-supplemented medium. The assay used a one-step addition to induce cell lysis and generate a luminescent signal proportional to the amount of ATP present, which is directly proportional to the number of metabolically active cells present in culture.

Each compound evaluated was prepared as a DMSO stock solution (10 mM). Compounds were tested in duplicate on each plate, with an 11-point serial dilution curve (1:3 dilution). Compound treatment (50 µL) was added from the compound dilution plate to the cell plate. The highest compound concentration was 1 or 10 µM (final), with a 0.3% final DMSO (#D-5879, Sigma, St Louis, MO) concentration. Plates were then incubated at 37° C., 5% CO$_2$. After 3-5 days of compound treatment, CellTiter-Glo® Reagent (#G7573, Promega, Madison, WI) was prepared in one of two ways. If thawing a frozen aliquot of CellTiter-Glo® Reagent, the aliquot was thawed and equilibrated to RT prior to use while keeping it protected from light. Alternatively, new bottles of CellTiter-Glo® Buffer and CellTiter-Glo® Substrate were thawed and equilibrated to RT prior to use. CellTiter-Glo® Buffer (100 mL) was transferred into the amber bottle containing CellTiter-Glo® Substrate to reconstitute the lyophilized enzyme/substrate mixture, forming the CellTiter-Glo® Reagent. The reconstituted reagent was mixed by gently inverting the contents to obtain a homogeneous solution, and went into solution easily in less than 1 min. Any unused reconstituted CellTiter-Glo® Reagent was immediately aliquoted and frozen at −20° C., and protected from light. Cell plates were equilibrated at RT for approximately 30 mins. An equi-volume amount of CellTiter-Glo® Reagent (100 µL) was added to each well. Plates were mixed for 2 mins on an orbital shaker to induce cell lysis, and then were allowed to incubate at RT for 10 mins to stabilize the luminescent signal. Luminescence was recorded using the PerkinElmer EnVision Excite Multilabel Reader used for endpoint reading for luminescence detection (Waltham, MA). Data was analyzed using a four-parameter fit in Microsoft Excel.

Compounds of Formula (I) were active in this assay as provided in Table 2, where A=IC$_{50}$≤50 nM; B=IC$_{50}$>50 nM and <300 nM; and C=IC$_{50}$≥300 nM.

TABLE 2

| Example # | H1975 (nM) | PC9 (nM) | A431 (nM) |
|---|---|---|---|
| 1 | A | A | C |
| 2 | B | B | C |
| 3 | A | A | B |
| 4 | C | C | C |
| 5 | A | B | C |
| 6 | C | C | C |
| 7 | A | C | C |
| 8 | A | A | C |

Example D

Metabolite Identification in Hepatocytes of Mouse Rat, Dog and Human

Suspended hepatocytes in enough incubation medium to yield ~1.5×10⁶ cells/mL. Pipetted 199 μL of viable hepatocytes or the boiled hepatocytes into each wells of a 96-well non-coated plate. Placed the plate in the incubator on an orbital shaker to allow the hepatocytes to warm for 10 minutes. Pipetted 1 μL of the 2 mM test compound(s) into respective wells of the 96-well non-coated plate to start the reaction with final concentration of 10 μM. Returned the plate to the incubator and placed on an orbital shaker. Incubated at 37° C., 5% $CO_2$ and 90-95% relative humidity with shaking at 500 rpm on the shaker for 240 min. After incubation, transferred media from each well to a tube containing 400 μL cold methanol, washed the well with 200 μL cold methanol and then transferred the media to the corresponding tube. Centrifuged tubes for 10 minutes at 16,000 g. Aliquots of 200 μL of the supernatants were mixed with 200 μL of pure water and used for LC-MS/MS analysis. UHPLC-MS/MS analysis was conducted using a Dionex UltiMate 3000 UHPLC system (Thermo Fisher Scientific, USA) and Thermo Scientific Q Exactive (Thermo Fisher Scientific, USA) fitted with a HESI probe. Data was acquired using Xcaliur® v3.0 software (Thermo Fisher Scientific) and processed using Xcaliur® v3.0 software (Thermo Fisher Scientific) and Metworks® vi.3 software (Thermo Fisher Scientific), and metabolite was elucidated by Mass Frontier@ v7.0 predictive fragmentation software (Thermo Fisher Scientific).

As shown by the results in Table 3, the compound of Example 1 did not lead to the formation of the less selective metabolite AZ5104 in human hepatocyte cells.

TABLE 3

Metabolite Identification study: formation of AZ5104 via de-alkylation on the indole ring.

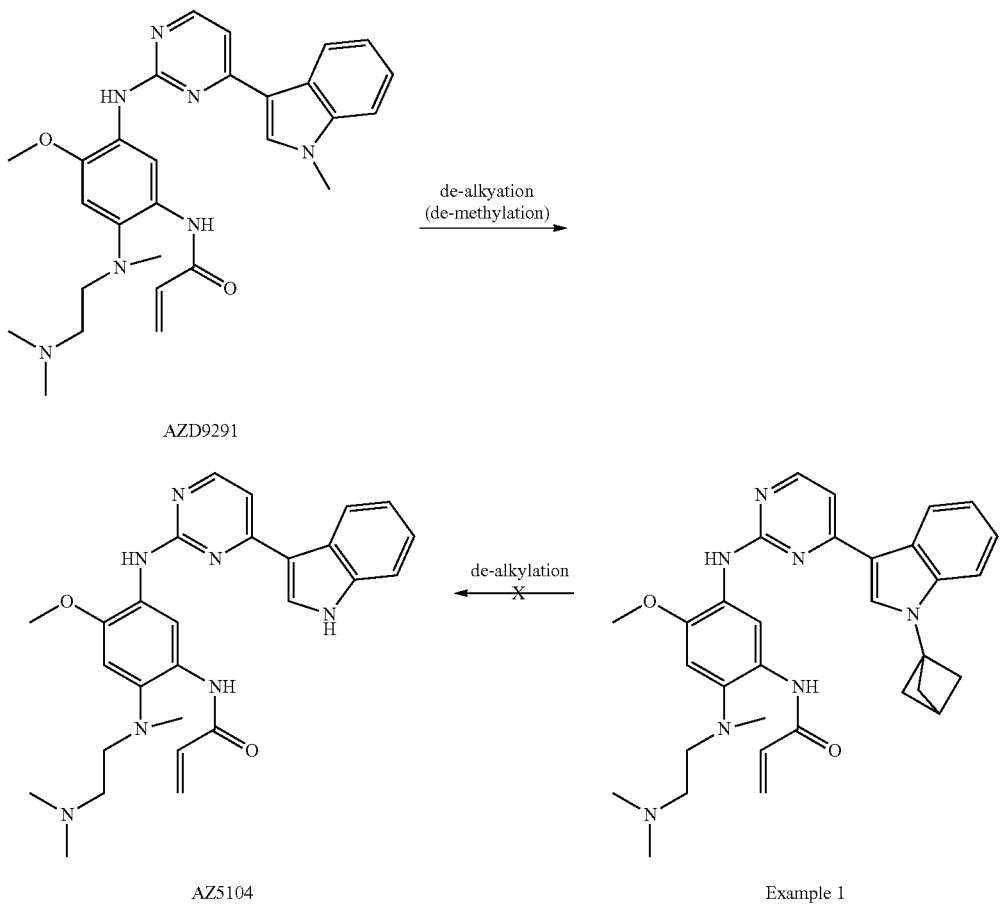

| Compound Incubated in hepatocytes | Metabolite AZ5104 | | | |
|---|---|---|---|---|
| | Mouse | Rat | Dog | Human |
| AZD9291 | — | — | — | Observed |
| Example 1 | Not observed | Not observed | Not observed | Not observed |

Inhibition of wild-type EGFR (WT EGFR) has been shown to cause side effects such as rash and diarrhea. AZ5104, a major human metabolite of AZD9291, is oberserved both in vitro and in vivo. AZ5104 is a more potent inhibitor of WT EGFR compared to AZD9291 as demonstrated by the data in Table 4. This difference in potency between AZD9291 and AZ5104 is believed to account and/or contribute to the clinical side effects of diarrhea (42%) and rash (41%) observed with AZD9291 treatment. As AZ5104 is not observed as a metabolite of the compound of Example 1, compounds of Formula (I), and pharmaceutically acceptable salts thereof, have fewer side effects (e.g., rash and/or diarrhea) and/or the severity of the side effect(s) is to a lesser degree.

TABLE 4

In vitro and in vivo data for AZD9291 and its metabolite AZ5104*

| Compound | WT EGFR CellI $C_{50}$ (nM) | H1975 Cell $IC_{50}$ (nM) | Mouse exposure | Human exposure |
|---|---|---|---|---|
| AZD9291 | 480 | 15 | — | — |
| AZ5104 | 33 | 2 | Roughly 10% of AZD9291 exposure | Roughly 10% of AZD9291 exposure |

*Data from Raymond et al., J. Med. Chem. (2014) 57(20):8249-8267 and Cross et al., Cancer Discovery, (2014) 4(9):1046-1061

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, wherein Formula (I) has the structure:

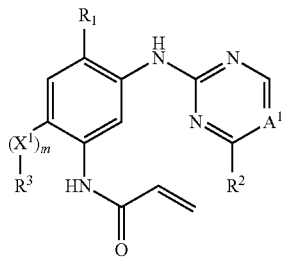

$R^1$ is selected from hydroxy and an unsubstituted $C_{1-4}$ alkoxy;

$R^2$

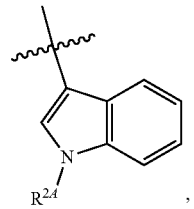

wherein $R^{2A}$ is an unsubstituted bicyclo pentyl, a fluoro-substituted bicyclo pentyl, a chloro-substituted bicyclo pentyl or a cyano-substituted bicyclo pentyl; and wherein $R^2$ is optionally substituted with one or more substituents independently selected from halogen, cyano, an unsubstituted $C_{1-4}$ alkyl, an unsubstituted $C_{1-4}$ haloalkyl, an unsubstituted $C_{1-4}$ alkoxy, an alkyl substituted mono-substituted amine and an alkyl substituted di-substituted amine;

$R^3$ is a substituted $C_{1-4}$ alkyl, wherein $R^3$ is substituted with $-(CR^{6A}R^{6B})_n NR^{7A}R^{7B}$;

$X^1$ is $NR^4$;

$R^4$ is selected from hydrogen and an unsubstituted $C_{1-4}$ alkyl;

$R^{6A}$ and $R^{6B}$ are each hydrogen;

$R^{7A}$ and $R^{7B}$ are independently selected from hydrogen and an unsubstituted $C_{1-4}$ alkyl;

$A^1$ is $CR^8$;

$R^8$ is selected from hydrogen, fluoro, chloro and cyano;

m is 1; and n is 0 or 1.

2. The compound of claim 1, wherein $R^2$ is

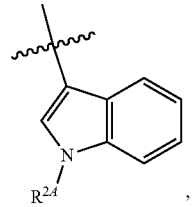

wherein $R^{2A}$ is an unsubstituted bicyclo pentyl.

3. The compound of claim 1, wherein $R^2$ is

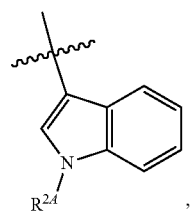

wherein $R^{2A}$ is a fluoro-substituted bicyclo pentyl, a chloro-substituted bicyclo pentyl or a cyano-substituted bicyclo pentyl.

4. The compound of claim 1, wherein $R^4$ is an unsubstituted $C_{1-4}$ alkyl.

5. The compound of claim 4, wherein $R^4$ is methyl.

6. The compound of claim 1, wherein $R^3$ is a substituted $C_2$ alkyl substituted by $-(CR_{6A}R^{6B})$, $NR_{7A}R_{7B}$.

7. The compound of claim 6, wherein n is 0.

8. The compound of claim 7, wherein $R^{7A}$ and $R^{7B}$ are each an unsubstituted $C_{1-4}$ alkyl.

9. The compound of claim 8, wherein the unsubstituted $C_{1-4}$ alkyl is methyl.

10. The compound of claim 1, wherein $R^1$ is an unsubstituted $C^{1-4}$ alkoxy; and $R^8$ is hydrogen.

11. The compound of claim 10, wherein the unsubstituted $C_{1-4}$ alkoxy is methoxy.

12. The compound of claim 1, wherein the compound is:

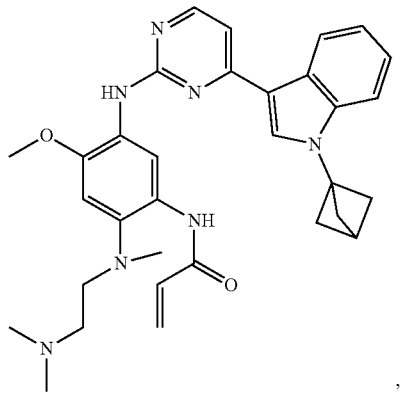 [SMILES: C=CC(=O)Nc1cc(Nc2nccc(-c3cn(C45CC(C4)C5)c4ccccc34)n2)c(OC)cc1N(C)CCN(C)C]

or a pharmaceutically acceptable salt thereof.

13. A pharmaceutical composition comprising an effective amount of the compound of claim 1, or a pharmaceutically acceptable salt thereof, and a pharmaceutically acceptable carrier, diluent, excipient or combination thereof.

14. A method for ameliorating or treating a cancer comprising contacting a malignant growth or a tumor that is in a subject having the malignant growth or the tumor with an effective amount of a compound of claim 1, or a pharmaceutically acceptable salt thereof, wherein the malignant growth or tumor is due to a cancer selected from a lung cancer, a pancreatic cancer, a colon cancer, a breast cancer, a prostate cancer, a head and neck cancer, an ovarian cancer, a brain cancer and a kidney carcinoma.

15. A method for inhibiting replication of a malignant growth or a tumor comprising contacting the growth or the tumor with an effective amount of a compound of claim 1, or a pharmaceutically acceptable salt thereof, wherein the malignant growth or tumor is due to a cancer selected from a lung cancer, a pancreatic cancer, a colon cancer, a breast cancer, a prostate cancer, a head and neck cancer, an ovarian cancer, a brain cancer and a kidney carcinoma.

16. A method for inhibiting the activity of EGFR comprising providing an effective amount of a compound of claim 1, or a pharmaceutically acceptable salt thereof, to a subject or sample having a cancer cell selected from a lung cancer cell, a pancreatic cancer cell, a colon cancer cell, a breast cancer cell, a prostate cancer cell, a head and neck cancer cell, an ovarian cancer cell, a brain cancer cell and a kidney carcinoma cell, and wherein the EGFR has one or more selected from a deletion in exon 19, an insertion in exon 20, a mutation at L858R and an acquired EGFR T790M mutation.

17. The compound of claim 1, wherein the compound is

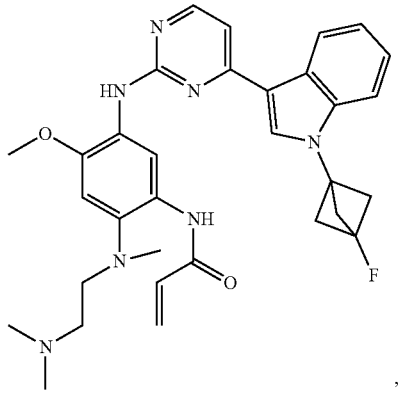 [SMILES: C=CC(=O)Nc1cc(Nc2nccc(-c3cn(C45CC(F)(C4)C5)c4ccccc34)n2)c(OC)cc1N(C)CCN(C)C]

or a pharmaceutically acceptable salt thereof.

18. The compound of claim 1, wherein the compound is

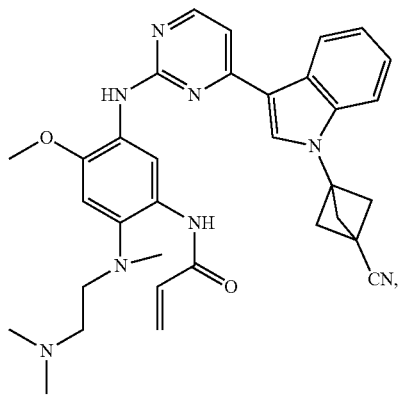 [SMILES: C=CC(=O)Nc1cc(Nc2nccc(-c3cn(C45CC(C#N)(C4)C5)c4ccccc34)n2)c(OC)cc1N(C)CCN(C)C]

or a pharmaceutically acceptable salt thereof.

19. The compound of claim 1, wherein the compound is

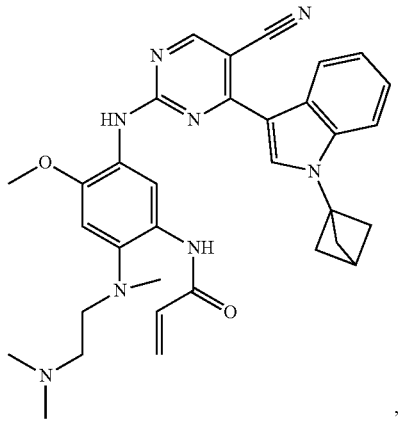 [SMILES: C=CC(=O)Nc1cc(Nc2ncc(C#N)c(-c3cn(C45CC(C4)C5)c4ccccc34)n2)c(OC)cc1N(C)CCN(C)C]

or a pharmaceutically acceptable salt thereof.

20. The compound of claim 1, wherein the compound is
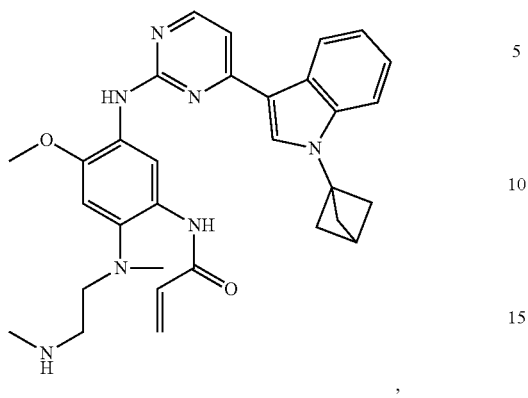
or a pharmaceutically acceptable salt thereof.
* * * * *